United States Patent [19]
Ono et al.

[11] Patent Number: 5,908,762
[45] Date of Patent: Jun. 1, 1999

[54] TRANSCRIPTION FACTOR REGULATING MHC EXPRESSION CDNA AND GENOMIC CLONES ENCODING SAME AND RETROVIRAL EXPRESSION CONSTRUCTS THEREOF

[75] Inventors: Santa Jeremy Ono, Baltimore, Md.; Jack L. Strominger, Lexington, Mass.

[73] Assignee: The Johns Hopkins University, Cambridge, Mass.

[21] Appl. No.: 08/828,584

[22] Filed: Mar. 31, 1997

Related U.S. Application Data

[62] Division of application No. 08/327,832, Oct. 21, 1994.

[51] Int. Cl.⁶ .............................. C12P 21/00; C12N 5/10; C12N 15/12; C07H 21/04
[52] U.S. Cl. .................. 435/69.1; 435/367; 435/372; 435/372.3; 435/6; 536/23.5; 536/24.31
[58] Field of Search .............................. 536/23.5, 24.31; 435/6, 69.1, 325, 367, 372, 372.3

[56] References Cited

U.S. PATENT DOCUMENTS

| | | | |
|---|---|---|---|
| 4,399,216 | 8/1983 | Axel et al. .................................. | 435/6 |
| 4,446,128 | 5/1984 | Baschang et al. .................... | 424/194.1 |
| 5,166,059 | 11/1992 | Pastan et al. .......................... | 435/69.7 |

OTHER PUBLICATIONS

Noelle, et al., "Regulation of the expression of multiple class II genes in murine B cells by B cell stimulatory factor–1 (BSF–1)," *J. Immunol.*, 137:1718–1723 (1986).
Boss, et al., "Regulation of a transfected human class II major histocompatibility complex gene in human fibroblasts," *Proc. Natl. Acad. Sci. USA*, 83:9139–9143 (1986).
Miwa, et al., "Sequence–specific interactions of nuclear factors with conserved sequences of human class II major histocompatibility complex genes," *Proc. Natl. Acad. Sci. USA*, 84:4939–4943 (1987).
Didier, et al., "Characterization of the cDNA encoding a protein binding to the major histocompatibility complex class II Y box," *Proc. Natl. Acad. Sci. USA*, 85:7322–7326 (1988).
Reith, et al., "Congenital immunodeficiency with a regulatory defect in MHC class II gene expression lacks a specific HLA–DR promoter binding protein, RF–X," *Cell*, 53:897–906 (1988).
Latron, et al., "Active suppression of major histocompatibility complex class II gene expression during differentiation from B cells to plasma cells," *Proc. Natl. Acad. Sci. USA*, 85:2229–2233 (1988).
Ono, et al., "Interferon–γ induces transcription and differential expression of MHC genes in rat insulinoma cell line RINm5F," *Diabetes*, 38:911–916 (1989).
Reith, et al., "MHC class II regulatory factor RFX has a novel DNA–binding domain and a functionally independent dimerization domain," *Genes & Dev.*, 4:1528–1540 (1990).
Liou, et al., "A new member of the leucine zipper class of proteins that binds to the HLA–DRα promoter," *Science*, 247:1581–1584 (1990).

Kara, et al., "A cDNA for a human Cyclic AMP Response Element–binding protein which is distinct from CREB and expressed preferentially in brain," *Mol. Cell. Biol.*, 10:1347–1357 (1990).
Andersson, et al., "NF–X2 that binds to the DRA X2–box is activator protein 1. Expression cloning of c–Jun," *J. Immunol.*, 145:3456–3462 (1990).
Benoist, et al., "Regulation of major histocompatibility complex class–II genes: X, Y and other letters of the alphabet," *Annu. Rev. Immunol.*, 8:681–715 (1990).
Klemsz, et al., "The macrophage and B cell–specific transcription factor PU.1 is related to the ets oncogene," *Cell*, 61:113–124 (1990).
Ono, et al., "Human X–box–binding protein 1 is required for the transcription of a subset of human class II major histocompatibility genes and forms a heterodimer with c–fos," *Proc. Natl. Acad. Sci. USA*, 88:4309–4312 (1991).
Ono, et al., "An isotype–specific trans–acting factor is defective in a mutant B cell line that expresses HLA–DQ, but not –DR or –DP," *J. Exp. Med.*, 173:629–637 (1991).
***Cogswell, et al., "Transcriptional regulation of the HLA–DRA gene," *Crit. Rev. Immunol.*, 11:87–112 (1991).
Ono, et al., "Transcription of a subset of human class II major histocompatibility complex genes is regulated by a nucleoprotein complex that contains c–fos or an antigenically related protein," *Proc. Natl. Acad. Sci. USA*, 88:4304–4308 (1991).
Viville, et al., "The Eα promoter: a linker–scanning analysis," *J. Immunol.*, 146:3211–3217 (1991).
Kara, et al., "In vivo footprinting of MCH class II genes: Bare promoters in the Bare Lymphocyte Syndrome," *Science*, 252:709–712 (1991).

(List continued on next page.)

*Primary Examiner*—George C. Elliott
*Assistant Examiner*—Robert Schwartzman
*Attorney, Agent, or Firm*—Banner & Witcoff, Ltd.

[57] ABSTRACT

The present invention relates to NF-X1, a novel DNA binding protein which regulates expression of major histocompatibility complex (MHC) class II molecules, and to DNA sequences which encode the protein as well as recombinant expression of the protein. NF-X1 is a newly identified, cysteine-rich polypeptide which interacts sequence-specifically with the conserved X1 box regulatory element found in the proximal promoters of class II MHC genes. A cysteine-rich domain within NF-X1 contains a motif repeated seven times, and this entire region is necessary and sufficient for both sequence specific binding and effector function. The motif is related to but distinct from the previously described metal-binding protein families: LIM domain and RING finger. NFX.1 mRNA is markedly overexpressed late after induction of cells with interferon-gamma, and this overexpression coincides with a reduction in the level of HLA-DRA transcript in these cells. Overexpression of this protein strongly and specifically represses the transcription of the HLA-DRA gene in MHC class II positive cell lines, indicating that the NF-X1 protein is a transcriptional repressor of MHC class II molecules.

11 Claims, 19 Drawing Sheets

OTHER PUBLICATIONS

Wright, et al., "In vivo footprint analysis of the HLA–DRA gene promoter: Cell–specific interaction at the octamer site and up–regulation of X box binding by interferon γ," *Proc. Natl. Acad. Sci. USA*, 89:7601–7605 (1992).

Glimcher, et al., "Sequences and factors: a guide to MHC class–II transcription," *Annu. Rev. Immunol.*, 10:13–49 (1992).

Li, et al., "Intro–exon organization of the NF–Y genes. Tissue–specific splicing modifies an activation domain," *J. Biol. Chem.*, 267:8984–8990 (1992).

Zeleznik–Le, et al., "The B cell–specific nuclear factor OTF–2 positively regulates transcription of the human class II transplantation gene, DRA," *J. Biol. Chem.*, 267:7677–7682 (1992).

Steimle, et al., "Complementation cloning of an MHC class II transactivator mutated in hereditary MHC class II deficiency (or Bare Lymphocyte Syndrome)," *Cell* 75:135–146 (1993).

Steimle, et al., "Regulation of MHC class II expression by interferon–γ mediated by the transactivator gene CIITA," *Science*, 265:106–109 (1994).

Brand, et al., "Characterization of a "silencer" in yeast: a DNA sequence with properties opposite to those of a transcriptional enhancer," *Cell*, 41:41–48 (1985).

Goodbourn, et al., "The human β–interferon gene enhancer is under negative control," *Cell*, 45:601–610 (1986).

***Ma, et al., "The carboxy–terminal 30 amino acids of GAL4 are recognized by GAL80," *Cell*, 50:137–142 (1987).

Gaul, et al., "Analysis of Krüppel protein distribution during early Drosophila development reveals posttranscriptional regulation," *Cell*, 50:639–647 (1987).

Keller, et al., "Identification of an inducible factor that binds to a positive regulatory element of the human β–interferon gene," *Proc. Natl. Acad. Sci. USA*, 85:3309–3313 (1988).

Baeuerle, et al., "IκB: A specific inhibitor of the NFκB transcription factor," *Science*, 242:540–546 (1988).

Levine, et al., "Transcriptional repression of eukaryotic promoters," *Cell*, 59:405–408 (1989).

Drouin, et al., "Glucocorticoid receptor binding to a specific DNA sequence is required for hormone–dependent repression of pro–opiomelanocortin gene transcription," *Mol. Cell. Biol.*, 9:5305–5314 (1989).

Freyd, et al., "Novel cysteine–rich motif and homeodomain in the product of the *Caenorhabditis elegans* cell lineage gene lin–11", *Nature*, 344:876–879 (1990).

Licht, et al., "*Drosophila* Krüppel protein is a transcriptional repressor," *Nature*, 346:76–79 (1990).

Driggers, et al., "An interferon γ–regulated protein that binds the interferon–inducible enhancer element of major histocompatibility complex class I genes," *Proc. Natl. Acad. Sci. USA*, 87:3743–3747 (1990).

***Whittemore, et al., "Postinduction repression of the β–interferon gene is mediated through two positive regulatory domains," *Proc. Natl. Acad. Sci. USA*, 87:7799–7803 (1990).

Freemont, et al., "A novel cysteine–rich sequence motif," *Cell*, 64:483–484 (1991).

Keller, et al., "Identification and characterization of a novel repressor of β–interferon gene expression," *Gene & Dev.*, 5:868–879 (1991).

Keller, et al., "Only two of the five zinc fingers of the eukaryotic transcriptional repressor PRDI–BF1 are required for sequence–specific DNA binding," *Mol. Cell. Biol.*, 12:1940–1949 (1992).

Desjarlais, et al., "Use of zinc–finger consensus sequence framework and specificity rules to design specific DNA binding proteins," *Proc. Natl. Acad. Sci. USA*, 90:2256–2260 (1993).

Song, "A Novel Cysteine–Rich Sequence–Specific DNA–Binding Protein Interacts with the Conserved X–Box Motif of the Human MHC Class II Genes and Functions as a Transcriptional Repressor," *FASEB J.*, 8(4–5) Abstract A519, 1994.

Song, "A Novel Cysteine–Rich Sequence–Specific DNA–Binding Protein Interacts with the Conserved X–Box Motif of the Human Major Histocompatibility Complex Class II Genes Via a Repeated Cys–His Domain and Functions as a Transcriptional Repressor," *J. Exp. Med.*, 180:1763–1774 (1994).

Zhang, "The Major Histocompatibility Complex Class II Promoter–Binding Protein RFX (NF–X) is a Methylated DNA–Binding Protein," *Mol. Cell. Biol.*, 13:(11):6810–6818 (1993).

Bonas, "Genetic and Structural Characterization of the Avirulence Gene AvrBs3 from *Xanthomonas campestris* pv. *vesicatoria,*" *Mol. Gen. Genet*, 218:127–136 (1989).

Yanagawa, "A Novel Sodium Channel Inhibitor from *Conus georgraphus*: Purification, Structure, and Pharmacological Properties," *Biochemistry*, 27:6256–6262 (1988).

```
ATGGAATTCAGCAGCATCTGTATTGAATTT AAAAGTACCTTGAGACAGGAGGGCCCTCCG CCATCCGTGCCGCAGAACCTGAGTCGAGC      90
MetGluPheSerSerIleCysIleGluPhe LysSerThrLeuArgGlnAlaGluProPro  ProSerArgArgAlaGluProArgSerSer

TGTACAGTTCACCACCTCCCTGTCACCTTT CCAGGCAGGTCCCTTATGATGAAATCTCTG CTGTTCATCAGCATAGTTATCATCCGTCAG     180
CysThrValHisHisLeuProValThrPhe ProGlyArgSerLeuMetMetLysSerLeu  LeuPheIleSerIleValIleIleArgGln

GAAGGCAAACCTAAGAGTCAGCAGACGTCT TTCCAGTCCTCTCCTTGTAATAAATCGCCC AAGAGCCATGCCCTTCAGAATCAACCTTGG     270
GluGlyLysProLysSerGlnGlnThrSer PheGlnSerSerProCysAsnLysSerPro  LysSerHisGlyLeuGlnAsnGlnProTrp

CAGAAATTGAGGAATGAGAAGCACCATATC AGAGTCAAGAAAGCACAGAGTCTTGCTGAG CAGACCTCAGATACAGCTGGATTCAGGAGC     360
GlnLysLeuArgAsnGluLysHisHisIle ArgValLysLysAlaGlnSerLeuAlaGlu  GlnThrSerAspThrAlaGlyLeuGluSer

TCGACCAGATCAGAGAGTGGGACAGACCTC AGAGAGCATAGTCCTTCTGAGAGTGAGAAG GAAGTGTGGGTGCAGATCCCAGGGGACCA     450
SerThrArgSerGluSerGlyThrAspLeu ArgGluHisSerProSerGluSerGluLys  GluValValGlyAlaAspProArgGlyAla

AAACCCAAAAAGCACACAGTTTGTATAC AGCTATGGTAGAGGACCAAAAGTCAAGGAG AAACTCAAATGTGAATGGAGTAACCGAACA       540
LysProLysLysAlaThrGlnPheValTyr SerTyrGlyArgGlyProLysValLysGlu  LysLeuLysCysGluTrpSerAsnArgThr

ACTCCAAAACCGGAGATGCTGGACCCCAAA GTACCAAACCTGTGGGGTTTCCACCCTG ACTCTTCAGAGGCATCCTCTAGAAAGGAG       630
ThrProLysProGluMetLeuAspProLys ValProAsnLeuTrpGlyPheSerThrLeu  ThrLeuGlnArgHisProLeuGluLysGlu

TATTGGATGGTATGAGCCAGACGAAATG AGCAGAGAAGATACCCACAGAAAAGGCCTC CCTGGGAAGTGAGTGGAGGGCCAGCCAGAC       720
TyrTrpMetGlyMetGluProAspGluMet SerArgGluAspThrHisArgLysGlyLeu  ProGlyLysTrpArgGlyProGlyHisAsp
```

FIG.2A-1

```
CAGGCAGAAATCCACCAAACAGGAGGCC  ACCGACATACAAACGCAGGACACAGAAACA  ACATGGGCCCCATTCCAAAGTGATGACCTC     810
GlnAlaGluIleHisGlnAsnArgArg  Ala  ThrAspIleGlnThrArgGluThr  ThrTrpAlaProPheGlnSerAspAspLeu

AATGAAAGACCAGCCAAAATCTACCTGTGAC  AGTGAGAACTTGGCAGTCATCAACAAGTCT  TCCAGGAGGGTTGACCAAGAGAAATGCACT    900
AsnGluArgProAlaLysSerThrCysAsp  SerGluAsnLeuAlaValIleAsnLysSer  SerArgArgValAspGlnGluLysCysThr

GTACGGAGGCAGGATCCTCAAGTAGTATCT  CCTTTCTCCCGAGGCCAAACAGAACCATGTG  CTAAAGAATGTGGAAACGCACACAGGTTCT    990
ValArgArgGlnAspProGlnValValSer  ProPheSerArgGlyLysGlnAsnHisVal  LeuLysAsnValGluThrHisThrGlySer

CTAATTGAACAACTAACACAGAAAAATAC  GAGTGCATGGTGTGCTGTGAATTGGTTCGT  GTCACGGCCCCAGTGTGGAGTTGTCAGAGC    1080
LeuIleGluGlnLeuThrGlnLysTyr  GluCysMetValCysCysGluLeuValArg  ValThrAlaProValTrpSerCysGlnSer

TGTTACCATGTGTTTCATTTGAACTGCATA  AAGAAATGGGCCAAGGTCTCCAGCCATCTCAA  GCAGATGGCCAGAGTGGTTGGAGGTGCCCT   1170
CysTyrHisValPheHisLeuAsnCysIle  LysLysTrpAlaArgSerProAlaSerGln  AlaAspGlyGlnSerGlyTrpArgCysPro

GCCTGTCAGAATGTTTCTGCACATGTTCCT  AATACCTTCTCTGTTTCTGTGCAAGGTA  AAGAATCCTGAGTGGAGCAGAAATGAAATT    1260
AlaCysGlnAsnValSerAlaHisValPro  ValThrAlaProValTrpSerCysGlnSer  CysTyrHisValPheHisLeuAsnCysIle

CCACATAGCTGTGGTGAGGTTTGTAGAAAG  AAACAGCCTGCCCAGGACTGCCCACATTCC  TGTAACCTTCTCTGCCATCCAGGACCCTGC    1350
ProHisSerCysGlyGluValCysArgLys  LysGlnProGlyGlnAspCysProHisSer  CysAsnLeuLeuCysHisProGlyProCys

CCACCCTGCCCTGCCTTTATGACAAAACA  TGTGAATGTGGACGAACCAGGCACACAGTT  CCGTGGTCAGGCTGTCTCAGTCCACTGT     1440
ProProCysProAlaPheMetThrLysThr  CysGluCysGlyArgThrArgHisThrVal  ArgCysGlyGlnAlaValSerValHisCys
```

FIG.2A-2

```
TCTAACCCATGTGAGAATATTTGAACTGT GGTCAGCACCAGTGTGCTGAGCTGTGCCAT GGGGGTCAGTGCCAGCCTTGCCAGATCATT    1530
SerAsnProCysGluAsnIleLeuAsnCys GlyGlnHisGlnCysAlaGluLeuCysHis  GlyGlyGlnCysGlnProCysGlnIleIle

TTGAACCAGGTATGCTATTGCGGCAGCACC TCCCGAGATCTCTTATGTGTGGAACCGATGTA GGAAAGTCTGATGGATTTGGGATTTCAGC    1620
LeuAsnGlnValCysTyrCysGlySerThr SerArgAspIleLeuTyrValGlyThrAspVal GlyLysSerAspGlyPheGlyAspPheSer

TGTTTAAAGACATGTGGCAAGGACTTGAAA TGCGGTAACCATACATGTTCGCAAGTGTGC  CACCCTCAGCCTGCCAGCAATGCCCACGG     1710
CysLeuLysThrCysGlyLysLysAspLeuLys CysGlyAsnHisThrCysSerGlnValCys HisProGlnProCysGlnProCysProArg

CTCCCCCAGCTGGTGCCGTGTTGCCCCTGT GGCCAAACTCCTCAGCCAATTGCTAGAA CTTGGAAGTAGTACGGAAAACATGATG      1800
LeuProGlnLeuValArgCysCysProCys GlyGlnThrProLeuSerGlnLeuLeuGlu LeuGlySerSerArgLysThrCysMet

GACCCTGCCTTCATGTGGAAAAGTGTGC GGCAAGCCTCTGCCTTGTGGTTCCTTAGAT TTCATTCATACCTGTGAAAAGCTCTGCCAT    1890
AspProValProSerCysGlyLysValCys GlyLysProLeuProCysGlySerLeuAsp PheIleHisThrCysGluLysLeuCysHis

GAAGGAGACTGTGGACCAGTCTCTCCACA TCAGTTATTTCCTGCAGATGTCTTTCAGA ACAAAGGAGCTTCCATGTACCAGTCTCAAA   1980
GluGlyAspCysGlyProValSerArgThr SerValIleSerCysArgCysArgSerPheArg ThrLysGluLeuProCysThrSerLeuLys

AGTGAAGATGCTACATTTATGTGTGACAAG CGGTGTAACAAGAAACGGTTGTGTGGACCG CATAAATGTAATGAGATATGCTGTGGAT   2070
SerGluAspAlaThrPheMetCysAspLys ArgCysAsnLysLysArgLeuCysGlyArg HisLysCysAsnGluIleCysCysValAsp

AAGGAGCACAAGTGTCTTTGATTTGTGG AGGAAACTCCGTTGTGGCCTTCATAGGTGT GAAGAACCTTGTCATCGTGGAAACTGCCAG   2160
LysGluHisLysCysLeuIleCysGly ArgLysLeuArgCysGlyLeuHisArgCys GluGluProCysHisArgGlyAsnCysGln
```

FIG.2A-3

```
ACATGCTGGCAAGCCAGTTTTGATGAATTA ACCTGCCATTGTGGTGCATCAGTGATTAC CCTCCAGTTCCCTGTGGTACTAGGCCCCT    2250
ThrCysTrpGlnAlaSerPheAspGluLeu ThrCysHisGlyAlaSerValIleTyr    ProProValProCysGlyThrArgProPro

GAATGTACCCAAACCTGCCTAGAGTCCAT GAGTGTGACCATCCAGTATATCATTCTTGT CATAGTGAGGAGAAGTGTCCCCTTGCACT    2340
GluCysThrGlnThrCysAlaArgValHis GluCysAspHisThrCysTyrHisSerCys HisSerGluGluLysCysProProCysThr

TTCCTAACTCAGAAGTGGTGCATGGGCAAG CATGAGTTTCCGGAGCAACATCCCCTGT CAC CTGGTTGATATCTCTTGCGGATTACCCTGC    2430
PheLeuThrGlnLysTrpCysMetGlyLys HisGluPheArgSerAsnIleProCysHis LeuValAspIleSerCysGlyLeuProCys

AGTGCCACGCTACCATGTGGGATGCACAAA TGTCAGAGACTCTGTCACAAAGGGAGTGT CTTGTGATGAGCCCTGCAAGCAGCCCTGC    2520
SerAlaThrLeuProCysGlyMetHisLys CysGlnArgLeuCysHisLysGlyValCys LeuValAspProCysLysGlnProCys

ACCACCCCCAGAGCTGACTGTGGTCACCCG TGTATGGCACCCTGCCATACCAGCTCACCC TGCCCCTGTGACTGCTTGTAAAGCTAAGGTA    2610
ThrThrProArgAlaAspCysGlyHisPro CysMetAlaProCysHisThrSerSerPro CysProValThrAlaCysLysAlaLysVal

GAGCTACAGTGT GAATGTGGACGAAGAAAA GAGATGGTGATTTGCTCTGAAGCATCCATG ACTTATCAAAGATAGTCCAATCTCCATG    2700
GluLeuGlnCys GluCysGlyArgArgLys GluMetValIleCysSerGluAlaSerMet ThrTyrGlnArgLeuAlaAlaIleSerMet

GCCTCTAAGATAACAGACATGCAGCTTGGA GGTTCAGTGGAGATCAGCAAGTTAATTACC AAAAAGGAAGTTCATCAAGCCAGGCTGGAG    2790
AlaSerLysIleThrAspMetGlnLeuGly GlySerValGluIleSerLysLeuIleThr LysLysGluValHisGlnAlaArgLeuGlu

TGTGATGAGGAGTGTTCAGCCTTGGAAAGG AAAAAGAGATTAGCAGAGGCATTCATATC AGTGAGGATTCTGATCCTTTCAATATACGT    2880
CysAspGluGluCysSerAlaLeuGluArg LysLysArgLeuAlaGluAlaPheHisIle SerGluAspSerAspProPheAsnIleArg
```

FIG.2A-4

```
TCTTCAGGGTCAAAATTCAGTGATAGTTTG AAAGAAGATGCCAGGAAGGACTTAAAGTTT GTCAGTGACGTTGAGAAGGAAATGGAAACC     2970
 SerSerGlySerLysPheSerAspSerLeu LysGluAspAlaArgLysAspLeuLysPhe ValSerAspValGluLysGluMetLguThr

CTCGTGGAGCCGTGAATAAGGCAAAGAAT AGTAAGAAAGCCACAGCTTCCCTCCCATG AACAGAGACCACCGCGGATCATCCATGAC     3060
 LeuValGluAlaValAsnLysGlyLysAsn SerLysLysSerHisSerPheProProMet AsnArfAspHisArfArfIleIleHisAsp

TTGGCCCAAGTTTATGCCTGGAGAGCGTG AGCTATGACACTGAACCCGAAGCGCAATGTG GTGGTCACTGCCATCAGGGGAAGTCCGTT     3150
 LeuAlaGlnValTyrGlyLeuGluSerVal SerTyrAspSerGluProLysArgAsnVal ValValThrAlaIleArgGlyLysSerVal

TGTCCTCCTACCACGGCTGACAGGTGTGCTT GAAAGGGAAATGCAGGCACGGGCCTCCACCA CCGATTCCTCATCACAGACATCAGTCAGAC   3240
 CysProProThrThrLeuThrGlyValLeu GluArgGluMetGlnAlaArgProProPro ProIleProHisHisArgHisGlnSerAsp

AAGAATCCTGGGAGCAGTAATTTACAGAAA ATAACCAAGGAGCCAATAATTGACTATTTT GACGTCCAGGACTAAGAGATCATGATGCA     3330
 AspValGlnAsp

CTTAGATAAAAGAATGATTAGGTATAGTGG AGACTTATTTGCCAGCAGATAAATCATGCC CGTTCCCCTCTGCCTGGCAGAATCACAGAC     3420

TCACATACTGTCTTGTACTGACACATCCAA AGCATGAGTGTGTCAGAAATCCCTTGTCTA TTCCTGTCTGTATAAAGTGTTTCAGGATGA     3510

AAAAAAAAAAAAAAAAAAAAAAAAAAAAAA AAA                                                            3543
```

FIG.2A-5

NFX REPEATS

| | | | | | | | |
|---|---|---|---|---|---|---|---|
| 417/473: | RNEIPHSCGEVCRKKQPGQDCP | ------ | HSCNLLCHPGPCPPCPAFMTKTCECGRTRH |
| 473/521: | GQAVSVHCSNPCENILNCGQ | ------ | HQCAELCHGGQCQPCQIILNQVCYCGSTS |
| 533/583: | SDGFGDFSCLKXCGKDLKCGN | ------ | HTCSQVCHPQPCQQCPRLPQLVRCCPCGQT |
| 599/647: | CMDPVPSCGKVCGKPIPCGSLDFIHTCEKLCHEGDCGPVSRTSVISCRC |
| 688/737: | CVDKEHKCPLICGRKLRCGL | ------ | HRCEEPCHRGNCQTCWQASFDELTCHCGAS |
| 799/839: | CHLVDISCGLPCSATLPCGM | ------ | HKCQRLCHKGECLVDEPCKQP |
| 840/890: | | CTTPRADCG | ------ | HPCMAPCHTSSPCPVTACKAKVELQCECGRRKEMVICSEASS |

CONSENSUS:

| C | SC | CG | L CG | H C | LCH G CQPC | VC C |
|---|---|---|---|---|---|---|
| 3 | 35 | 53 | 5 76 | 7 7 | 477 5 6344 | 33 5 |

FIG.2D

RNASE PROTECTION ANALYSIS

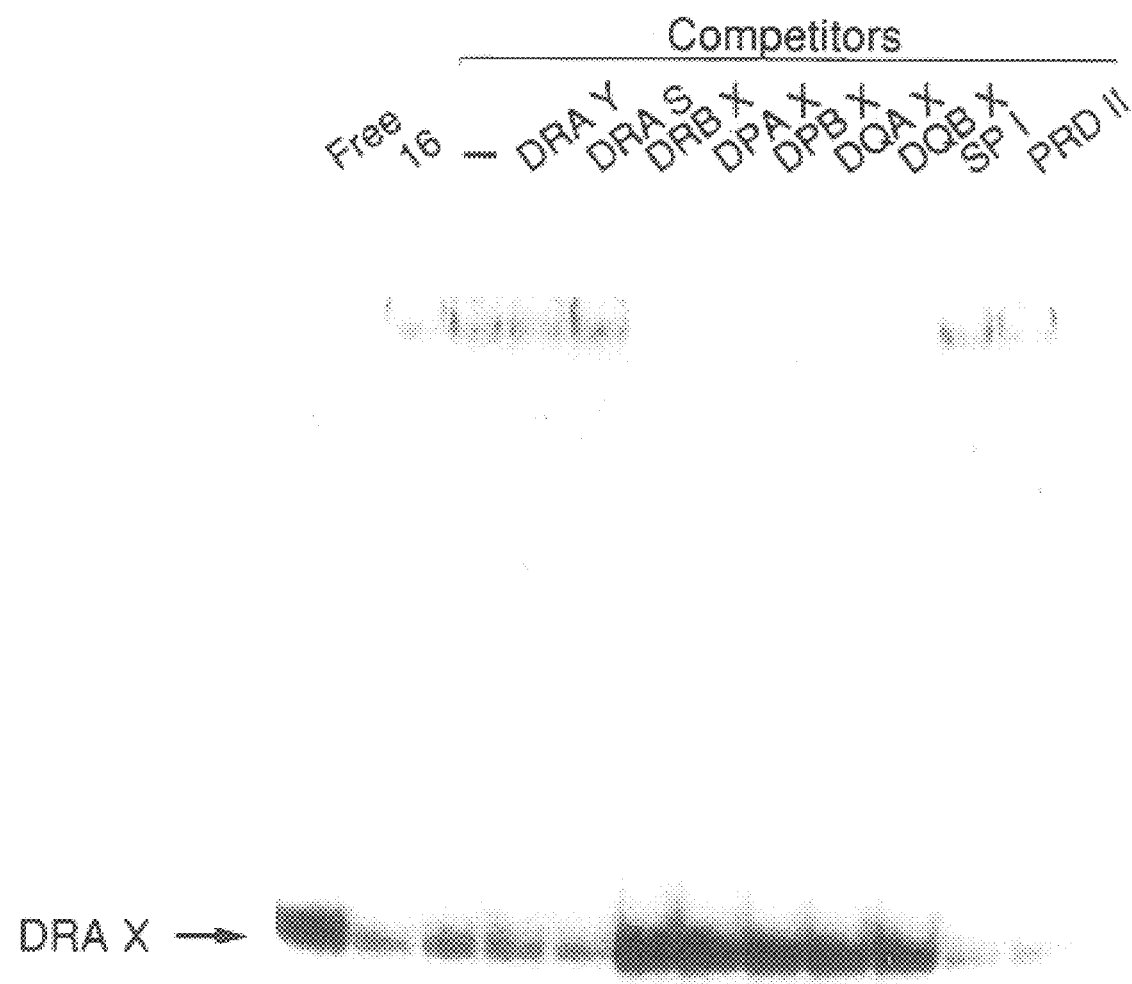

TRANSCRIPTION FACTOR REGULATING MHC EXPRESSION CDNA AND GENOMIC CLONES ENCODING SAME AND RETROVIRAL EXPRESSION CONSTRUCTS THEREOF

This application is a division of application Ser. No. 08/327,832, filed Oct. 21, 1994.

The work leading to this invention was supported in part by Grant Nos. 5R32 DK 30241-08 and S07RR05378 from the National Institutes of Health. The U.S. Government retains certain rights in this invention.

BACKGROUND OF THE INVENTION

1. Field of the Invention

The present invention relates to a novel DNA binding protein which regulates expression of major histocompatibility complex (MHC) class II molecules, DNA sequences which encode the protein, and recombinant expression of the protein.

2. Review of Related Art

Expression of class II major histocompatibility complex (MHC) molecules is usually restricted to cells of the immune system, and dysregulated expression is hypothesized to contribute to the pathogenesis of a severe combined immunodeficiency syndrome and certain autoimmune diseases. As most mammalian cells can endocytose and process foreign antigen, the critical determinant of an antigen presenting cell is its ability to express class II MHC molecules. The class II MHC molecules function in the presentation of processed peptides to helper T cells.

The class II region of the human major histocompatibility complex encodes three heterodimeric molecules: HLA-DR, -DQ and -DP, composed of alpha and beta chain polypeptides with an approximate Mr of 60,000. These highly polymorphic molecules determine the ability of an individual to respond to a given antigen, and the molecular basis of this ability lies in the differential capacity of allelic forms of these molecules to bind particular peptides. Peptides derived from extracellular antigens are recognized by helper T cells in the context of these molecules.

Due to the central role these molecules play in the initiation of the immune response, considerable effort is focused on elucidating the mechanisms governing the proper tissue-specific and developmental regulation of the class II MHC genes (Benoist, et al., 1990, Ann. Rev. Immunol., 8:681; Ono, et al., 1991, J. Exp. Med., 173:629). These molecules are expressed constitutively on professional antigen-presenting cells such as macrophages, dendritic cells and B cells, and their biosynthesis is inducible on other cells upon binding of certain lymphokines, such as interferon-gamma, interleukin-4 and tumor necrosis factor alpha, to their respective receptors (Noelle, et al., 1986, J. Immunol., 137:1718; Glimcher, et al., 1992, Ann. Rev. Immunol., 10:13). Class II MHC genes are inactive in plasma cells, and cell fusion experiments indicate that a dominant repressor protein actively inhibits transcription of these genes (Latron, et al., 1988, Proc. Natl. Acad. Sci., USA, 85:2229).

Expression of the class II MHC genes is controlled primarily at the transcriptional level (Ono, et al., 1989, Diabetes, 7:911; Ting, J.P.Y., 1991, Crit. Rev. Immunol., 11:87). Systematic deletion and mutagenesis of the proximal promoters of the human and murine class II genes have identified two highly conserved cis-acting elements called the X and Y boxes that bind several transcription factors that participate in the regulation of these genes (Boss, et al., 1986, Proc. Natl. Acad. Sci., USA, 83:9139; Miwa, et al., 1987, Proc. Natl. Acad. Sci., USA, 84:4939; Viville, et al., 1991, J. Immunol., 146:3211; Klemsz, et al., 1990, Cell, 61:113). These regions are occupied by DNA-binding proteins in class II positive cells but not in class II negative or in certain Bare Lymphocyte Syndrome cell lines (Kara, et al., 1991, Science, 252:709; Wright, et al., 1992, Proc. Natl. Acad. Sci., USA, 89:601).

The X-box is further subdivided into an upstream X1 box [5'CCTAGCAACAGATG3'](SEQ ID NO:6) and an X2 box [5'CGTCATC3'](SEQ ID NO:7) located immediately 3' of the X1 box (Latron, et al., 1988). A family of genes encoding X1 box binding proteins have been cloned (RFX1-5) and at least one of these, RFX5, appears to be required for class II MHC gene transcription (Reith, et al., 1988, Cell, 53:897; Reith, et al., 1990, Genes Dev., 4:1528). At least three factors (hXBP1, hXBP2, and c-jun) can interact directly with the X2 box, with the product of the c-fos proto-oncogene being a likely partner (Liou, et al., 1990, Science, 247:1581; Kara, et al., 1990, Mol. Cell. Biol., 10:1347; Anderson, et al., 1990, J. Immunol., 145:3456; Ono, et al., 1991, Proc. Natl. Acad. Sci. USA, 88:4309; Ono, et al., 1991, Proc. Natl. Acad. Sci. USA, 88:4304).

The Y box is in fact an inverted CCAAT box which can bind a multiplicity of factors. Two factors: YB-1 and NF-Y have been implicated in class II MHC gene regulation. YB-1 appears to encode a potent repressor of interferon-gamma induced class II gene expression, while the heterodimeric NF-Y encodes an activator (Didier, et al., 1988, Proc. Natl. Acad. Sci. USA, 85:7322; Zeleznik-Le, et al., 1992, J. Biol. Chem., 267:7677; Li, et al., 1992, J. Biol. Chem., 267:8984). The Y-box may therefore act as a bifunctional cis-element, binding both an activator and repressor of class II MHC gene expression.

Recently, a novel factor (CIITA) required for both constitutive and interferonγ mediated expression of all of the class II MHC genes has been isolated by complementation cloning using a mutant B-lymphoblastoid cell line (Steimle, et al., 1993, Cell, 75:135; Steimle, et al., 1994, Science, 265:106). This factor does not appear to interact directly with the class II MHC proximal promoter, but CIITA transactivation is mediated by the proximal promoter (presumably via protein-protein interactions between CIITA and other class II promoter binding proteins).

A series of classical genetic studies by Accolla and coworkers have previously demonstrated multiple genetic loci that encode either activators or repressors of class II MHC gene expression (reviewed in Glimcher, et al., 1992; Latron, et al., 1988). These studies predicted the existence of two classes of genes termed aIr-1 and sIr-1 that encode either activator(s) or silencer(s) of class II MHC gene expression, respectively. The newly isolated cDNA (CIITA, located on human chromosome 16) appears to encode aIr-1 (Steimle, et al., 1993; Steimle, et al., 1994).

The sIr-1 gene or genes were identified in cell fusion experiments, where factors expressed in the class II negative plasmacytoma cell line P3-U1 were shown to rapidly and dominantly repress class II MHC transcription in the human B cell line Raji. However, neither the sIr-1 gene nor its gene product have been isolated. Since the conserved X1 box of class II MHC genes plays a critical role in the transcriptional regulation of these genes, there is a need for methods of obtaining, in isolated form, the product of the sIr-1 locus.

SUMMARY OF THE INVENTION

It is an object of this invention to provide a substantially pure polypeptide which specifically binds the X1 regulatory region of the genes for MHC class II proteins.

It is another object of this invention to provide a nucleotide sequence encoding a protein which binds to the X1 box motif and for recombinant production of the protein.

These and other objects are achieved by one or more of the following objects of this invention.

In one embodiment, this invention provides a substantially pure polypeptide which contains at least about five copies of a cysteine rich sequence according to SEQ ID NO:1 coupled to a cysteine rich sequence according to SEQ ID NO:2 by a bridge peptide of from one to five amino acids, this polypeptide specifically binding to the X1 box motif, a double stranded DNA having a sequence according to SEQ ID NO:3. In a particular embodiment, the sequence of this polypeptide is selected from the group consisting of NF-X1, muteins of NF-X1, truncations of NF-X1, and fusion proteins containing them.

In another embodiment, this invention provides chimeric DNA molecules comprising a region corresponding to NFX.1 or to a DNA sequence encoding a polypeptide selected from the group consisting of muteins of NF-X1, truncations of NF-X1, and fusion proteins containing them, the polypeptide specifically binding to the X1 box motif. This invention also provides a cell population transformed with such DNA molecules, the population preferably being substantially free of cells not transformed with the DNA molecule.

In still another embodiment, the invention provides a method of producing a polypeptide which contains at least about five copies of a cysteine rich sequence according to SEQ ID NO:1 coupled to a cysteine rich sequence according to SEQ ID NO:2 by a bridge peptide of from one to five amino acids, the polypeptide specifically binding to the X1 box motif, by growing a population of cells transformed with chimeric DNA molecules encoding the polypeptide under conditions whereby the polypeptide encoded by the chimeric DNA is expressed, and preferably excreted, and recovering the polypeptide.

In yet another embodiment, this invention provides a method for determining the presence of a polynucleotide substantially homologous to a coding sequence for NF-X1, by incubating a sample suspected of containing the polynucleotide with a nucleotide probe having a sequence complementary to a single stranded DNA molecule comprising at least 20 sequential nucleotides, the sequential nucleotides making up a subsequence of NFX.1 or a DNA sequence complementary thereto, under conditions where the probe will form hybrids with nucleic acid from the sample, and detecting nucleic acid hybrids.

In still another embodiment, this invention provides an antibody reactive with an epitope on NF-X1. The invention also provides a method for determining the presence of NF-X1 in a sample, the sample being preferably a crude cell or tissue extract, by incubating the sample with an antibody specifically immunologically reactive with NF-X1 polypeptide and detecting immunocomplex formation. Preferably the antibodies provided with this invention will react with one of the following peptides found in the NF-X1 sequence (SEQ ID NO:5): Glu-Arg-Lys-Lys-Arg-Ala (residues 939–944 of NF-X1), Lys-Glu-Asp-Ala-Arg-Lys-Asp (residues 971–977), and Ser-Glu-Ser-Glu-Lys-Glu (residues 136–141). Alternatively, the invention provides a method for determining the presence of anti-NF-X1 antibodies in a biological sample, by incubating the sample with NF-X1 polypeptides and detecting immunocomplex.

In yet another method, this invention provides a method for suppressing expression of major histocompatibility complex (MHC) class II component proteins by transfecting cells with an expression vector encoding NF-X1 polypeptide.

This invention provides a substantially pure preparation of a newly identified, cysteine-rich polypeptide which interacts sequence-specifically with the conserved X1 box regulatory element found in the proximal promoters of class II MHC genes and molecularly cloned complementary DNA encoding this polypeptide. The cysteine-rich domain contains a motif repeated seven times, and this entire region is necessary and sufficient for both sequence specific binding and effector function. The motif is related to but distinct from the previously described metal-binding protein families: LIM domain and RING finger.

Overexpression of this protein strongly and specifically represses the transcription of the HLA-DRA gene in the MHC class II positive cell line Raji, and inhibits induction of the gene in the inducible cell line HeLa by inter-feron-gamma, strongly suggesting that the NF-X1 protein is a transcriptional repressor. Additional evidence that NFX.1 encodes a biologically relevant repressor of HLA-DRA gene expression stems from the finding that the NFX.1 mRNA is markedly overexpressed late after induction of HeLa cells with interferon-gamma, and that this overexpression coincides with a reduction in the level of HLA-DRA transcript in these cells. The identification of NF-X1 indicates that the X1 element, like the Y-box, can bind factors that can either activate or repress class II MHC gene expression.

BRIEF DESCRIPTION OF THE FIGURES

FIGS. 2A-1 through 2A-5 and 2B through 2E show the deduced amino acid sequence and primary structural analysis of the NF-X1 polypeptide. A) The complete deduced amino acid sequence (SEQ ID NO:5) of the largest open reading frame of the NFX.1 mRNA (SEQ ID NO:4) is shown from the first in frame methionine to the most ORF-proximal polyadenylation site. B) Primary structure analysis of NF-X1. The entire amino acid sequence was subdivided into 22 fragments of 50 residues and subjected to computer analysis. Salient features are summarized below. C) Hydropathy plot for the deduced amino acid sequence of NF-X1 using the algorithm of Kyte and Doolittle. D) Amino acid homology alignment of the seven repeated domains within the cysteine-rich region(SEQ ID NO:5). E) Location of potential sites of post-translational modification (glycosylation, phosphorylation, myristylation).

FIGS. 4A, 4B and 4C(A) through 4C(G) show that NF-X1 is a binding protein specific for the sequence of the X1 box and that NF-X1 requires its cysteine-rich domain for DNA-binding. A) Electrophoretic mobility shift analysis of recombinant NF-X1showing that recombinant NF-X1 forms a specific complex with a double-stranded, DRA X1 box oligonucleotide. B) Truncated forms of the NF-X1 cDNA were generated using the indicated restriction endonucleases. The relative positions of each fragment relative to the open reading frame are indicated. C) In situ binding of induced fusion proteins encoded by λ1gt11 bacteriophage clones harboring the truncated NF-X1 polypeptides shown in B.

DETAILED DESCRIPTION OF THE EMBODIMENTS

Definitions

Figure 1:
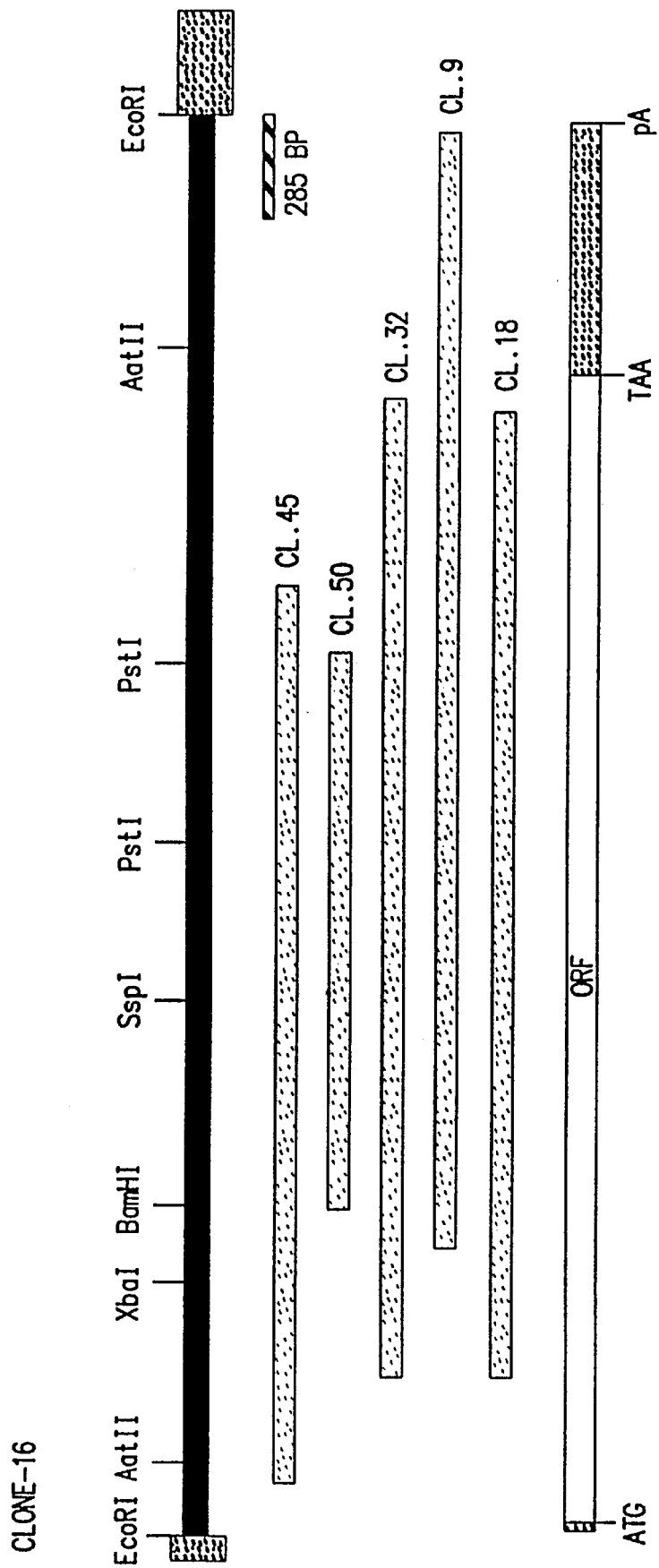
FIG. 1 shows overlapping lambda-gt11 cDNA clones encoding NF-X1, restriction map of clone-16 and NF-X1 mRNA structure.

In describing the present invention, the following terminology is used in accordance with the definitions set out below.

Nucleic Acids

A "double-stranded DNA molecule" refers to the polymeric form of deoxyribonucleotides (adenine, guanine, thymine, or cytosine) in its normal, double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed stand of DNA (i.e., the strand having a sequence homologous to the mRNA).

A DNA sequence "corresponds" to an amino acid sequence if translation of the DNA sequence in accordance with the genetic code yields the amino acid sequence (i.e., the DNA sequence "encodes" the amino acid sequence).

One DNA sequence "corresponds" to another DNA sequence if the two sequences encode the same amino acid sequence.

Two DNA sequences are "substantially homologous" when at least about 85% (preferably at least about 90%, and most preferably at least about 95%) of the nucleotides match over the defined length of the DNA sequences. Sequences that are substantially homologous can be identified in a Southern hybridization experiment under, for example, stringent conditions as defined for that particular system. Defining appropriate hybridization conditions is within the skill of the art. See "General Methods" below.

A "chimeric DNA" is an identifiable segment of DNA within a larger DNA molecule that is not found in association with the larger molecule in nature. Thus, when the chimeric DNA encodes a protein segment, the segment coding sequence will be flanked by DNA that does not flank the coding sequence in any naturally occurring genome. Allelic variations or naturally occurring mutational events do not give rise to a chimeric DNA as defined herein.

A coding sequence is an in-frame sequence of codons that (in view of the genetic code) correspond to or encode a protein or peptide sequence. Two coding sequences correspond to each other if the sequences or their complementary sequences encode the same amino acid sequences. A "coding sequence" in association with appropriate regulatory sequences may be transcribed and translated into a polypeptide in vivo. A polyadenylation signal and transcription termination sequence will usually be located 3' to the coding sequence. A "promoter sequence" is a DNA regulatory region capable of binding RNA polymerase in a cell and initiating transcription of a downstream (3' direction) coding sequence. A coding sequence is "under the control" of the promoter sequence in a cell when RNA polymerase which binds the promoter sequence transcribes the coding sequence into mRNA which is then in turn translated into the protein encoded by the coding sequence.

For purposes of defining the present invention, the promoter sequence is bounded at its 3' terminus by the translation start codon of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eucaryotic promoters will often, but not always, contain "TATA" boxes and "CAT" boxes. Procaryotic promoters contain Shine-Delgarno sequences in addition to the −10 and −35 consensus sequences.

A cell has been "transformed" by exogenous DNA when such exogenous DNA has been introduced inside the cell wall. Exogenous DNA may or may not be integrated (covalently linked) to chromosomal DNA making up the genome of the cell. In procaryotes and yeast, for example, the exogenous DNA may be maintained on an episomal element such as a plasmid. With respect to eukaryotic cells, a stably transformed cell is one in which the exogenous DNA has become integrated into a chromosome so that it is inherited by daughter cells through chromosome replication. This stability is demonstrated by the ability of the eukaryotic cell to establish cell lines or clones comprised of a population of daughter cells containing the exogenous DNA.

A "clone" is a population of cells derived from a single-cell or common ancestor by mitosis.

A "cell line" is a clone of a primary cell that is capable of stable growth in vitro for many generations.

A "replicon" is any genetic element (e.g., plasmid, chromosome, virus) that functions as an autonomous unit of DNA replication in vivo; i.e., capable of replication under its own control.

Vectors are used to introduce a foreign substance, such as DNA, RNA or protein, into an organism. Typical vectors include recombinant viruses (for DNA) and liposomes (for protein). A "DNA vector" is a replicon, such as plasmid, phage or cosmid, to which another DNA segment may be attached so as to bring about the replication of the attached segment.

An "expression vector" is a DNA vector which contains regulatory sequences which will direct protein synthesis by an appropriate host cell. This usually means a promoter to bind RNA polymerase and initiate transcription of mRNA, as well as ribosome binding sites and initiation signals to direct translation of the mRNA into a polypeptide. Incorporation of a DNA sequence into an expression vector at the proper site and in correct reading frame, followed by trans-formation of an appropriate host cell by the vector, enables the production of a protein encoded by said DNA sequence.

A "DNA library" is a population of vectors which each contain a DNA coding sequence for some protein. The population as a whole encodes a large number of peptides, and the sequence for a particular one of the peptides can be recovered from the library using an appropriate screening procedure.

In a "combinatorial library" DNA coding sequences from more than one DNA library are introduced into the vectors that make up the combinatorial library, so that each vector has at least one coding sequence from each of the original libraries.

"Amplification" of nucleic acid sequences is the in vitro production of multiple copies of a particular nucleic acid sequence. The amplified sequence is usually in the form of DNA. A variety of techniques for carrying out such amplification are described in a review article by Van Brunt (1990, *Bio/Technol.*, 8(4):291–294).

Polypeptides

Polypeptides are polymers made up of a sequence of amino acids linked by peptide bonds, containing at least 10 and usually 50 or more amino acids in the sequence. Proteins are polypeptides which usually have 35 or more amino acids and form a characteristic three dimensional structure (tertiary structure).

Two amino acid sequences are "substantially homologous" when at least about 90% of the amino acids match over the defined length of the amino acid sequences, preferably a match of at least about 92%, more preferably a match of at least about 95%.

One amino acid sequence "corresponds" to another amino acid sequence if at least 75% of the amino acid positions in the first sequence are occupied by the same amino acid residues in the second sequence. Preferably 90% of the amino acid positions are identical, and most preferably 95% of the amino acid positions are identical. Alternatively, two amino acid sequences are considered to correspond to each other if the differences between the two sequences involve only conservative substitutions.

"Conservative amino acid substitutions" are the substitution of one amino acid residue in a sequence by another residue of similar properties, such that the secondary and tertiary structure of the resultant peptides are substantially the same. Conservative amino acid substitutions occur when an amino acid has substantially the same charge as the amino acid for which it is substituted and the substitution has no significant effect on the local conformation of the protein. Amino acid pairs which may be conservatively substituted for one another are well-known to those of ordinary skill in the art.

The polypeptides of this invention encompass NF-X1 and NF-X1 analogs. NF-X1 is a naturally occurring, mature protein from mammalian cells, and further encompasses all precursors and allelic variations of NF-X1, as well as including forms of heterogeneous molecular weight that may result from inconsistent processing in vivo. An example of the NF-X1 sequence is shown in FIG. 2A. "NF-X1 analogs" are a class of peptides which includes:

1) "NF-X1 muteins," which are polypeptides which are substantially homologous to NF-X1. Preferably the amino acid sequence of the "mutein" differs from that of NF-X1 by 8 or fewer amino acid residues, more preferably, 7 or fewer residues, even more preferably about 5 or fewer residues and most preferably about 2 or fewer residues. It is sometimes preferred that any differences in the amino acid sequences of the two proteins involve only conservative amino acid substitutions. Alternatively, changes such as the elimination of cysteine which alter the activity or stability of the protein may be preferred.

2) "Truncated NF-X1 peptides," which include fragments of either "NF-X1" or "NF-X1 muteins" that preferably retain either (i) an amino acid sequence unique to NF-X1, (ii) an epitope unique to NF-X1 or (iii) NF-X1 activity. Most preferably, truncated NF-X1 peptides retain at least one 23–27 residue sequence corresponding to the cysteine-rich motif described below in reference to FIG. 2D.

3) "NF-X1 fusion proteins" include heterologous polypeptides which are made up of one of the above polypeptides (NF-X1, NF-X1 muteins or truncated NF-X1 peptides) fused to any heterologous amino acid sequence. Preferably such heterologous sequences are fused to the N-terminal end of the hu-MIP sequence and comprise a leader sequence to direct secretion.

"Unique" NF-X1 sequences, either amino acid sequences or nucleic acid sequences which encode them, are sequences which are identical to a sequence of a NF-X1 polypeptide, but which differ in at least one amino acid or nucleotide residue from the sequences of NFX.2 and NFX.3 (homologous genes found in the human genome) and RFX 1-5 (distinct X1-box binding proteins), and preferably, are not found elsewhere in the human genome. Similarly, an epitope is "unique" to NF-X1 polypeptides if it is found on NF-X1 polypeptides but not found on any members of the homologous gene family.

A composition comprising a selected component A is "substantially free" of another component B when component A makes up at least about 75% by weight of the combined weight of components A and B. Preferably, selected component A comprises at least about 90% by weight of the combined weight, most preferably at least about 99% by weight of the combined weight. In the case of a composition comprising a selected biologically active protein, which is substantially free of contaminating proteins (a "substantially pure" protein composition), it is sometimes preferred that the composition having the activity of the protein of interest contain species with only a single molecular weight (i.e., a "homogeneous" composition).

As used herein, a "biological sample" refers to a sample of tissue or fluid isolated from a individual, including but not limited to, for example, plasma, serum, spinal fluid, lymph fluid, the external sections of the skin, respiratory, intestinal, and genitourinary tracts, tears, saliva, milk, blood cells, tumors, organs, and also samples of in vivo cell culture constituents (including but not limited to conditioned medium resulting from the growth of cells in cell culture medium, putatively virally infected cells, recombinant cells, and cell components).

"Human tissue" is an aggregate of human cells which may constitute a solid mass. This term also encompasses a suspension of human cells, such as blood cells, or a human cell line.

The term "binding partner" as used herein refers to a molecule capable of binding a ligand molecule with high specificity, as for example an antigen and an antibody specific therefor. In general, the specific binding partners must bind with sufficient affinity to immobilize the analyte copy/complementary strand duplex (in the case of capture probes) under the isolation conditions. Specific binding partners are known in the art, and include, for example, biotin and avidin or streptavidin, IgG and protein A, the numerous known receptor-ligand couples, and complementary polynucleotide strands. In the case of complementary polynucleotide binding partners, the partners are normally at least about 15 bases in length, and may be least 40 bases in length; in addition, they generally have a content of Gs and Cs of at least about 40% and as much as about 60%. The polynucleotides may be composed of DNA, RNA, or synthetic nucleotide analogs.

The term "coupled" as used herein refers to attachment by covalent bonds or by strong non-covalent interactions (e.g., hydrophobic interactions, hydrogen bonds, etc.). Covalent bonds may be, for example, ester, ether, phosphoester, amide, peptide, imide, carbon-sulfur bonds, carbon-phosphorus bonds, and the like.

An "epitope" is a structure, usually made up of a short peptide sequence or oligosaccharide, that is specifically recognized or specifically bound by a component of the immune system. T-cell epitopes have generally been shown to be linear oligopeptides. Two epitopes correspond to each other if they can be specifically bound by the same antibody. Two antibodies correspond to each other if both are capable of binding to the same epitope, and binding of one antibody to its epitope prevents binding by the other antibody.

The term "immunoglobulin molecule" encompasses whole antibodies made up of four immunoglobulin peptide chains, two heavy chains and two light chains, as well as immunoglobulin fragments. "Immunoglobulin fragments" are protein molecules related to antibodies, which are known to retain the epitopic binding specificity of the original antibody, such as Fab, F(ab)'$_2$, Fv, etc.

Two polypeptides are "immunologically cross-reactive" when both polypeptides react with the same polyclonal antiserum.

General Methods

The practice of the present invention employs, unless otherwise indicated, conventional molecular biology, microbiology, and recombinant DNA techniques within the skill of the art. Such techniques are well known to the skilled worker and are explained fully in the literature. See, e.g., Maniatis, Fritsch & Sambrook, "Molecular Cloning: A Laboratory Manual" (1982); "DNA Cloning: A Practical Approach," Volumes I and II (D. N. Glover, ed., 1985); "Oligonucleotide Synthesis" (M. J. Gait, ed., 1984); "Nucleic Acid Hybridization" (B. D. Hames & S. J. Higgins, eds., 1985); "Transcription and Translation" (B. D. Hames & S. J. Higgins, eds., 1984); "Animal Cell Culture" (R. I. Freshney, ed., 1986); "Immobilized Cells and Enzymes" (IRL Press, 1986); B. Perbal, "A Practical Guide to Molecular Cloning" (1984), and Sambrook, et al., "Molecular Cloning: a Laboratory Manual" (1989).

DNA segments or oligonucleotides having specific sequences can be synthesized chemically or isolated by one of several approaches. The basic strategies for identifying, amplifying and isolating desired DNA sequences as well as assembling them into larger DNA molecules containing the desired sequence domains in the desired order, are well known to those of ordinary skill in the art. See, e.g., Sambrook, et al., (1989); B. Perbal, (1984). Preferably, DNA segments corresponding to NFX.1 may be isolated individually using the polymerase chain reaction (M. A. Innis, et al., "PCR Protocols: A Guide To Methods and Applications," Academic Press, 1990). A complete sequence may be assembled from overlapping oligonucleotides prepared by standard methods and assembled into a complete coding sequence. See, e.g., Edge (1981) Nature 292:756; Nambair, et al. (1984) Science 223:1299; Jay, et al. (1984) J. Biol. Chem., 259:6311.

The assembled sequence can be cloned into any suitable vector or replicon and maintained there in a composition which is substantially free of vectors that do not contain the assembled sequence. This provides a reservoir of the assembled sequence, and segments or the entire sequence can be extracted from the reservoir by excising from DNA in the reservoir material with restriction enzymes or by PCR amplification. Numerous cloning vectors are known to those of skill in the art, and the selection of an appropriate cloning vector is a matter of choice (see, e.g., Sambrook, et al., incorporated herein by reference). The construction of vectors containing desired DNA segments linked by appropriate DNA sequences is accomplished by techniques similar to those used to construct the segments. These vectors may be constructed to contain additional DNA segments, such as bacterial origins of replication to make shuttle vectors (for shuttling between prokaryotic hosts and mammalian hosts), etc.

Procedures for construction and expression of mutant proteins of defined sequence are well known in the art. A DNA sequence encoding a mutant form of NF-X1 can be synthesized chemically or prepared from the wild-type sequence by one of several approaches, including primer extension, linker insertion and PCR (see, e.g., Sambrook, et al.). Mutants can be prepared by these techniques having additions, deletions and substitutions in the wild-type sequence. It is preferable to test the mutants to confirm that they are the desired sequence by sequence analysis and/or the assays described below. Mutant protein for testing may be prepared by placing the coding sequence for the polypeptide in a vector under the control of a promoter, so that the DNA sequence is transcribed into RNA and translated into protein in a host cell transformed by this (expression) vector. The mutant protein may be produced by growing host cells transfected by an expression vector containing the coding sequence for the mutant under conditions whereby the polypeptide is expressed. The selection of the appropriate growth conditions is within the skill of the art.

The NFX.1 Nucleotide Sequence

The NFX.1 nucleotide sequence and the amino acid sequence it encodes (NF-X1) are shown in FIG. 2A and SEQ ID No. 4 and 5. The DNA sequence encoding NF-X1 can be synthesized chemically or isolated by one of several approaches. The complete sequence may be assembled from overlapping oligonucleotides prepared by standard methods and assembled into a complete coding sequence. See, e.g., Edge (1981) Nature 292:756; Nambair, et al. (1984) Science 223:1299; Jay, et al. (1984) J. Biol. Chem., 259:6311. The isolation methods will rely in part on nucleic acid hybridization using appropriate single stranded or double stranded nucleotide or oligonucleotide probes. Such probes can be constructed synthetically, based on the DNA or amino acid sequences disclosed herein, or isolated from genomic or cDNA clones also described herein.

Cloning the Nucleotide Sequence

Clones containing the DNA sequence of this invention can be obtained by those of ordinary skill in the art using well-known procedures. For instance, a library of mammalian (preferably human) DNA sequences may be constructed in any convenient vector (see, e.g., Sambrook, et al.), and then clones can be selected which hybridize with the cDNA sequence of NFX.1 (SEQ ID NO:4). Alternatively, a family of DNA probes representing degenerate sequences encoding amino acid sequences found in SEQ ID NO:5 may be constructed, and clones from the library selected on the basis of hybridization with these probes.

The basic strategies for preparing oligonucleotide probes and DNA libraries, as well as their screening by nucleic acid hybridization, are well known to those of ordinary skill in the art. See, e.g., Sambrook, et al., "Molecular Cloning: a Laboratory Manual" (1989); B. Perbal, "A Practical Guide To Molecular Cloning" (1984). First, a DNA library is prepared. The library can consist of a genomic DNA library from a human source. Human genomic libraries are known in the art. More preferred are DNA libraries constructed of cDNA, prepared from poly-A-plus RNA (mRNA) by reverse transcription. The mRNA is isolated from a cell line or tissue believed to express the protein cross-reactive with a peptide according to SEQ ID NO.5. A suitable source of mRNA for cDNA library constructions are the cell lines: Jurkat, HeLa, or Raji. The genomic DNA or cDNA is cloned into a vector suitable for construction of a library. The construction of an appropriate library is within the skill of the art. See, e.g., B. Perbal, supra. Once the library is constructed, oligonucleotides or amplified DNA fragments (e.g., fragments derived by PCR from the NF-X1 sequence) may be used to probe the library to identify the segment carrying a sequence encoding NF-X1.

Nucleic Acid Probes

Oligonucleotides can be designed and produced for use as hybridization probes to locate the other coding sequences. In general, the probes are synthesized chemically, preferably based upon known nucleic acid sequences, such as the sequences of the clones shown in FIG. 1 (which encode portions of the sequence for the entire protein shown in FIG. 2A). Ultimately, the isolated segments of DNA may be ligated together in such a way that the correct sequence of mature protein is encoded.

Nucleotide sequences are preferably selected so as to correspond to codons in FIG. 2A. By using a long probe (greater than 35 bp) it is possible to select sequences encoding NF-X1 which contain minor variations in the nucleotide sequence (see method of Lathe, R. (1985), J. Mol. Biol., 183:1–12, as discussed in Sambrook, et al.). In other cases, it may be desirable to use two sets of probes simultaneously, each to a different region of the gene.

While the exact length of any probe employed is not critical, typical probe sequences are no greater than 1000 nucleotides in length, more typically they are not greater than 500 nucleotides, even more typically they are no greater than 250 nucleotides; they may be no greater than 100 nucleotides, and also may be no greater than 75 nucleotides in length. Generally it is recognized in the art that probes from about 14 to about 20 base pairs are usually effective. Longer probe sequences may be necessary to encompass unique polynucleotide regions with differences sufficient to allow related target sequences to be distinguished. For this reason, probes are preferably from about 10 to about 100 nucleotides in length and more preferably from about 20 to about 50 nucleotides.

Selection of Clones

As is known in the art, oligonucleotide probes are usually labeled with a marker, such as a radionucleotide or biotin, using standard procedures. The labeled set of probes is then used in the screening step, which consists of allowing the single-stranded probe to hybridize to isolated single strand DNA (ssDNA) from the library, according to standard techniques. Either stringent or permissive hybridization conditions could be appropriate, depending upon several factors including, but not limited to, the length of the probe, whether the probe and library are from the same species, and whether the species are evolutionarily close or distant. It is within the skill of the art to optimize hybridization conditions so that homologous sequences are isolated and detectable above background hybridizations. The basic requirement is that hybridization conditions be of sufficient stringency so that selective hybridization occurs; i.e., hybridization is due to a minimum degree of nucleic acid homology (e.g., at least about 75%), as opposed to non-specific binding or hybridization due to a lower degree of homology. See generally, "Nucleic Acid Hybridization," (1985) B. D. Hames and S. J. Higgins, eds.

Where the library is an expression library, selection may be accomplished by expressing the library sequences and detecting the expressed peptides immunologically. Clones are selected which express peptides that bind antibodies reactive with NF-X1, prepared as described below. These selection procedures are well known to those of ordinary skill in the art (see, e.g., Sambrook, et al.).

A nucleic acid whose sequence corresponds to the sequence of NFX.1 may be used to select genomic clones corresponding to the NF-X1 gene. Alternatively, a nucleic acid whose sequence corresponds to the sequence of NFX.1 may be used to detect chromosomal alterations such as amplifications, translocations, deletions and mutations using fluorescent in situ hybridization, Southern blot analysis, dot blot analysis, the polymerase chain reaction, or semi-quantitative modifications of the polymerase chain reaction. Nucleic acids corresponding to the NF-X1 gene may be characterized by standard sequencing techniques and may also be used in any of the foregoing assays.

Selection based on Activity Assay: the CAT Assay System

Whether a given clone contains DNA sequences encoding regulatory function and effector domain(s) of NF-X1 in a may be demonstrated by cotransfection with two vectors: (1) a mammalian expression vector containing the sequence to be analyzed and (2) a reporter construct containing the HLA-DRA promoter operably linked to a reporter gene (such as the vector DRA300CAT in which expression of chloramphenicol acetyl transferase expression is under control of the HLA-DRA promoter). The DNA-binding domain of NF-X1 is capable of transcriptional repression of HLA-DRA mRNA, and expression vectors encoding truncated NF-X1 forms, specifically the cysteine-rich DNA binding domain, have been shown to be necessary and sufficient to mediate this transcriptional repression.

Figure 5A:
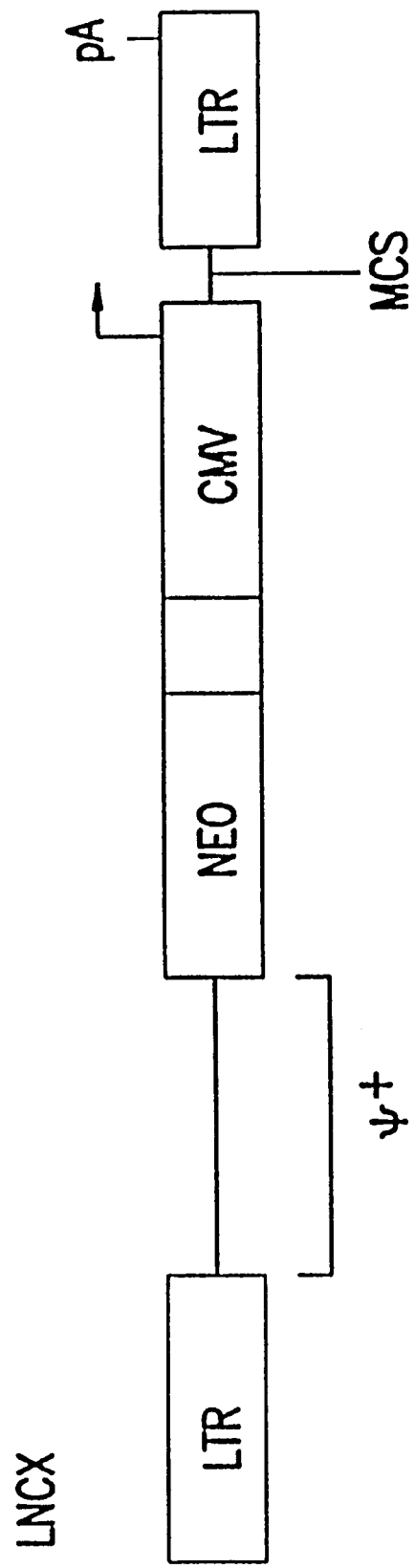
FIGS. 5A–C provide data which demonstrate that NFX.1 encodes a transcriptional repressor of HLA-DRA gene expression. A) Map of the eukaryotic retroviral expression vector-LNCX indicating the neomycin resistance gene for selection of stable transformants, the potent cytomegalovirus promoter, the multiple cloning site for insertion of NF-X1 cDNA and indicated subfragments, and the retroviral long terminal repeats. B) Histograms showing the CAT activity produced in the class II MHC positive cell line Raji and the class II inducible cell line HeLa after cotransfection with the HLA-DRA promoter reporter construct DRA300CAT and increasing amounts of the LNCX expression vectors containing the NF-X1 cDNA in either the sense or antisense orientations. C) Histograms showing CAT activity in Raji cells after cotransfection with DRA300CAT and expression vectors containing the previously described subfragments of the NF-X1 cDNA.

For example, expression vectors containing the DNA sequence to be tested may be generated by first subcloning the suspected NF-X1 restriction fragments in frame with the N-terminal peptide of the pRSET A,B,C series of expression vectors (Invitrogen) to provide an N-terminal methionine residue to each suspected NF-X1 subfragment. The resulting "expression cassettes" may then be subcloned utilizing PCR methods into the retroviral vector pLNCX (see FIG. 5A) to generate a series of mammalian expression vectors for cotransfection studies in mammalian cells. Each expression cassette can then be tested for its ability to direct the synthesis of the desired NF-X1 polypeptide by in vitro transcription and translation from linearized pRSET derivatives.

Cotransfection experiments where mammalian expression vectors, produced as described above, are cotransfected with the HLA-DRA reporter construct DRA300CAT into a series of class II positive, class II negative and gamma-interferon inducible cell lines may be used to assess whether a clone encodes a polypeptide having the regulatory function of NF-X1. Transfections may be performed using known methods, such as the DEAE dextran method or the lipofectamine reagent (Bethesda Research Laboratories) according to manufacturer's specifications. Typical transfections include varying amounts of effector plasmid (e.g., 1 to 15 $\mu$g) and of reporter construct (e.g., 1 to 5 $\mu$g) and tkHGH transfection control plasmid (for example, 5 $\mu$g). Cells are typically harvested by centrifugation 48 hours post-transfection, and washed twice. Extracts may then be prepared by multiple cycles of freeze/thaw, and CAT assays may be performed. (Each transfection experiment may be performed multiple times to calculate standard errors.)

Typically, histograms showing the CAT activity produced in the class II MHC positive cell line Raji after cotransfection with the HLA-DRA promoter reporter construct DRA300CAT and increasing amounts of expression vectors containing the suspected NF-X1 cDNA in either the sense or antisense orientations are compared to those for the class II inducible cell line HeLa. Wild-type NF-X1 has been found to encode a potent repressor of HLA-DRA transcription in the class II positive cell Raji. It also represses DRA transcription in interferon-gamma treated HeLa cells, but has no effect on DRA transcription in untreated HeLa cells and the class II negative T cell line Jurdat. CAT activities may be normalized by comparison with a cotransfected HGH expression vector. Expression of NF-X1 has no effect on transcription from reporter constructs that lack the X1 binding site such as a c-fos reporter construct, FC4, and RSVCAT, and these cell lines may be used for negative controls. See Example 6 below for an example of how this assay can be used to select clones having functional properties found in NF-X1.

Cloning for Expression

Once a coding sequence for the desired polypeptide sequence has been prepared or isolated, it can be cloned into any suitable vector or replicon and thereby maintained in a composition which is substantially free of vectors that do not contain the coding sequence (e.g., free of other clones from the library). Numerous cloning vectors are known to those of skill in the art, and the selection of an appropriate cloning vector is a matter of choice (see, e.g., Sambrook, et al., incorporated herein by reference). The DNA sequences and DNA molecules of the present invention may be expressed using a wide variety of host/vector combinations. According to the present invention, the coding sequence for the NFX.1 gene product is placed under the control of a promoter, ribosome binding site (especially for bacterial expression) and, optionally, an operator (collectively referred to herein as "control" elements), so that the DNA sequence is transcribed into RNA in the host cell transformed by a vector containing this expression construct. The coding sequence may or may not contain a signal peptide or leader sequence.

Of course, not all host/expression vector combinations function with equal efficiency in expressing the DNA sequences of this invention or in producing the polypeptides of this invention. However, a particular selection of a host/expression vector combination may be made by those skilled in the art. For example, the selection should be based on a balancing of a number of factors. These include compatibility of the host and vector, toxicity of the proteins encoded by the DNA sequence to the host, ease of recovery of the desired protein, expression characteristics of the DNA sequences and the expression control sequences operatively linked to them, biosafety, costs and the folding, form or any other necessary post-expression modifications of the desired protein. Preferably, the host cell will not express proteases which degrade the recombinant polypeptide of this invention.

Depending on the expression system and host selected, the protein is produced by growing host cells transformed by an expression vector containing the coding sequence for a polypeptide cross-reactive with the NFX.1 gene product under conditions whereby the protein is expressed. The protein is then isolated from the host cells and purified. The selection of the appropriate growth conditions and recovery methods are within the skill of the art.

Producing the Recombinant Peptide

Preferably, DNA from the selected clones should be subcloned into an expression vector, and the protein expressed by cells transformed with the vector should be tested for immunoreactivity with antibodies against the recombinant protein of this invention prepared as described below. Such subcloning is easily within the skill of the ordinary worker in the art in view of the present disclosure. The amino acid coding region of the DNA sequence of this invention may be longer or shorter than the coding region of the deposited vectors, so long as the recombinant peptide expressed by the DNA sequence retains at least one epitope cross-reactive with antibodies which are specifically immunoreactive with NF-X1 produced by the deposited strains. Preferably, the recombinant peptide will specifically bind to the X1 box (see procedure used in Example 1 below). Most preferably, the recombinant peptide will repress expression of genes operably-linked to the HLA-DRA promoter (see Example 6). The preparation of selected clones which contain DNA sequences corresponding to all or part of the sequence of NFX.1 may be accomplished by those of ordinary skill in the art using conventional molecular biology techniques along with the information provided in this specification and, optionally, the transformed cells deposited under ATCC Accession No. 75895.

It is possible to purify a protein cross-reactive with NF-X1 from an appropriate tissue/fluid source; however, a cross-reactive protein or polypeptide may also be produced by recombinant methods from a DNA sequence encoding such a protein or polypeptide. Polypeptides corresponding to the recombinant protein of this invention may be obtained by transforming cells with an expression vector containing DNA from a clone selected from an mammalian (preferably human) library as described above. Suitable expression vector and host cell systems are well known to those of ordinary skill in the art, and are taught, for instance, in Sambrook, et al., 1989. The peptide may be obtained by growing the transformed cells in culture under conditions wherein the cloned DNA is expressed. Of course, the peptide expressed by the clone may be longer or shorter than the NF-X1 so long as the peptides are immunologically cross-reactive. Preferred clones encode polypeptides which bind to X1 box DNA. Depending on the expression vector chosen, the peptide may be expressed as a fusion protein or a mature protein which is secreted or retained intracellularly, or as an inclusion protein. The desired polypeptides can be recovered from the culture by well-known procedures, such as centrifugation, filtration, extraction, and the like, with or without cell rupture, depending on how the peptide was expressed. The crude aqueous solution or suspension may be enriched for the desired peptide by protein purification techniques well known to those skilled in the art.

Characterization of NF-X1 Polypeptide

Human complementary DNA clones encoding a newly identified, cysteine-rich transcription factor, designated NF-X1, that binds to the conserved X-box motif of class II MHC genes have been obtained and the primary amino acid sequence has been deduced. (See FIG. 2A) The major open reading frame encodes a polypeptide of 1104 amino acids with a symmetrical organization. A central cysteine-rich portion encodes the DNA-binding domain, and is subdivided into seven repeated motifs. This motif is similar to but distinct from the LIM domain and the Ring finger family, and is reminiscent of known metal-binding regions. The unique arrangement of cysteines indicates that the consensus sequence: CX$_3$CX$_3$LXCGX$_{1-5}$HXCX$_3$CHXGXC(SEQ ID NOS:1 & 2) represents a novel cysteine-rich motif (see FIG. 2D).

Two lines of evidence indicate that the polypeptide encodes a potent and biologically relevant repressor of HLA-DRA transcription: 1) overexpression of NF-X1 from a retroviral construct strongly decreases transcription from the HLA-DRA promoter, and 2) the NFX.1 transcript is markedly induced late after induction with interferon-gamma, coinciding with post-induction attenuation of HLA-DRA transcription. Thus the protein encoded by NFX.1 appears to play an important role in regulating the duration of an inflammatory response, e.g., by limiting the period in which class II MHC molecules are induced by interferon-gamma.

Studies of the interaction of NF-X1 with other known class II MHC and general promoter binding proteins, will help to 1) elucidate how NF-X1 interacts sequence-specifically with the X1 element and 2) show how the effector function of NF-X1 is regulated in vivo. The three general models of how transcriptional repressors act include: a) direct competition for binding to a shared cis-element, b) silencing [position-independent repression] and c) neutralization [direct interaction with an essential activator], (Levine, et al., 1989, *Cell,* 59:405; Goodburn, et al., 1986, *Cell,* 45:601; Drouin, et al., 1989, *Mol. Cell. Biol.,* 2:5305; Brand, et al., 1985, *Cell,* 41:41; Licht, et al., 1990, *Nature,* 346:76; Ma, et al., 1987, *Cell,* 50:137; Baeuerle, et al., 1988, *Science,* 242:540). The molecular cloning of NF-X1 will allow determination of which of these three general mechanisms of transcriptional repression are operating at the X1 box.

NF-X1 availability will facilitate two lines of investigation with regard to regulation of effector function. First, an extensive analysis of NF-X1 expression will show when the NF-X1 gene product is overexpressed in other cell types or in response to physiological stimuli other than interferon-gamma. For example, the repressor of beta-interferon gene expression, PRDI-BF1, is involved in the postinduction turn-off of the gene (Whittemore, 1990, *Proc. Natl. Acad. Sci. USA,* 87:7799). PRDI-BF1 is therefore an example of a transcriptional repressor which binds to a positive regulatory element and is regulated by overexpression after the beta-interferon gene has been induced (Keller, et al., 1988, *Proc. Natl. Acad. Sci. USA,* 85:3309; Keller, et al., 1991, *Genes & Dev.,* 5:868). It is noteworthy that the class II MHC genes are also subject to postinduction turnoff after activation with interferon-gamma (Ono, et al., 1989). The NFX.1 protein appears to have a role in HLA-DRA transcription that has been induced by gamma-interferon similar to the role of PRDI-BF1 for beta-interferon expression. The second avenue of investigation involves the multiple sites of post-translational modification that may be involved in regulating effector function in other situations.

This information will contribute to the understanding of how class II MHC genes are regulated and will provide avenues to manipulate the expression of these genes in disease states. Specifically, retroviral vectors (such as those described herein) that can specifically repress the expression of class II MHC molecules will be useful as anti-inflammatory reagents. These studies will also provide insight into the general problem of how the relative influence of two proteins that bind to the same cis-element, but which have opposing regulatory function, can be determined.

Antibody Production

Antibodies which are specifically reactive with NF-X1 or the recombinant peptide of this invention may be obtained in a number of ways which will be readily apparent to those skilled in the art (see, e.g., Sanbrook et al.). The recombinant protein, obtained as described above can be injected into an animal as an immunogen to elicit polyclonal antibody production. Purification of the antibodies can be accomplished by selective binding from the serum, for instance by using recombinant NFX.1 polypeptide. The resultant polyclonal antisera may be used directly or may be purified by, for example, affinity absorption using recombinantly produced NF-X1 coupled to an insoluble support.

In another alternative, monoclonal antibodies specifically immunoreactive with the protein may be prepared according to well known methods (See, e.g., Kohler and Milstein, 1976, *Eur. J. Immunol.,* 6:611), using the peptide of this invention as an immunogen, using it for selection or using it for both functions. These and other methods for preparing antibodies that are specifically immunoreactive with the recombinant protein of this invention are easily within the skill of the ordinary worker in the art.

Preferred peptide fragments for use as immunogens in preparing either monoclonal or polyclonal antibodies are Glu-Arg-Lys-Arg-Ala(SEQ ID NO:14), Lys-Glu-Asp-Ala-Arg-Lys-Asp(SEQ ID NO:15), and Ser-Glu-Ser-Glu-Lys-Glu(SEQ ID NO:16). These peptide fragments usually are coupled to a larger molecule, such as bovine serum albumin or keyhole Limpet hemocyanin, when used as an immunogen or in subsequent affinity purification.

Diagnostic Assays

Detection of proteins cross-reactive with NF-X1, and their expression, may be on the nucleotide or peptide level. Antibodies can be prepared by immunizing mammals with peptides expressed from nucleic acid sequences corresponding to cross-reactive polypeptides, as indicated above, and selecting those antibodies specific to the NF-X1 using techniques that are well known to those skilled in the art. These antibodies can detect the presence of cross-reactive protein by a variety of immunoassay techniques. The nucleotide probe sequences provided herein can be used to detect expression of mRNA corresponding to cross-reactive proteins in accordance with any of the standard techniques. Expression may be detected either by in situ hybridization or by extraction and detection of mRNA. The particular procedures for gene probe assays and immunoassays are well-known to those skilled in the art.

Imunoassays

The antibodies of the present invention can be used to detect epitopes found on proteins cross-reactive with NF-X1 in histological sections of tissues including or not limited to: skin, muscle, heart, lung, pancreas, kidney, tonsil, liver, bone, intestine, brain, spleen and bladder. Tissues in which such epitopes are found are characterized in that nuclear immunoreactivity is observed without cytoplasmic staining.

One can detect antibody binding to tissue sections by any detection means known in the art for example, a radiolabel or a stain. A particularly useful stain employs peroxidase, hydrogen peroxide and a chromogenic substance such as aminoethyl carbazole. The peroxidase (a well known enzyme available from many sources) can be coupled to an anti-NF-X1 antibody or merely complexed via one or more antibodies to an antibody which specifically binds a protein which is cross-reactive with NF-X1. For example, a goat anti-peroxidase antibody and a goat anti-NF-X1 antibody can be complexed via an anti-goat IgG. Such techniques are well known in the art. Other chromogenic substances and enzymes may also be used. Radiolabeling of antibodies may also be used to detect antibody binding to sections. Labeled antibodies may be anti-NF-X1 or second antibodies immunoreactive with anti-NF-X1 antibodies. Again, such techniques are well known.

The precise technique by which a protein cross-reactive with the NFX.1 gene product is detected in patients is not critical to the invention. Biochemical or immunological techniques can be used which do not employ immunohistochemistry, although that is the preferred method of the present invention. Solution assay methods, including calorimetric, chemiluminescent or fluorescent immunoassays such as ELISA, sandwich and competitive immunoassays, immuno-diffusion, radio immunoassay, immunoelectrophoresis, Western blot and other techniques, may be used to detect and quantitate proteins cross-reactive with NF-X1 in a patient by preparing an extract of a tissue sample from the patient and assaying the extract.

A protein cross-reactive with the NFX.1 gene product can be quantitated in a biological fluid, such as serum, plasma, effusions, ascites, urine, cerebrospinal fluid, semen, breast aspirates and fluids of ovarian origin, using any detection means for NF-X1 described herein. Preferred methods employ immunological detection means. These include: radioimmunoassay, enzyme linked immunoadsorbent assay, complement fixation, nephelometric assay, immunodiffusion or immunoelectrophoretic assay and the like. Plasma should be anti-coagulated before use, as is known in the art. Cellular elements and lipid may be removed from fluids, e.g., by centrifugation. For dilute fluids, such as urine, protein may be concentrated, e.g., by ultra-filtration or salting-out.

Nucleotide Probe Assays for Expression

An elevated level of NF-X1 mRNA in a cell corresponds to elevated NF-X1 protein expression by the cell, and NF-X1 MRNA can be quantitated in a number of ways.

The nucleic acid probes described above for use in screening gene libraries and selecting clones may also be used to detect mRNA transcripts in cells that express a protein cross-reactive with the NFX.1 gene product. These probes preferably correspond to a sequence which encodes portions of the distinct sequences of NF-X1 (see FIGS. 2A, B and 4B). The probe can be either single or double stranded DNA or RNA. The size of a probe can vary from less than approximately 20 nucleotides to hundreds of nucleotides.

The most desirable nucleotide probes do not detect nucleotide sequences unrelated to their intended target, do not show significant homology with unrelated nucleotide sequences, and do not contain complementary sequences such that they would self-hybridize or fold upon themselves. The guanine and cytosine content of desirable probes is not so high as to promote non-specific hybridization with unrelated sequences rich in guanine and cytosine. Finally, the melting temperature and free energy of binding are generally favorably suited to the detection technique for which they are intended. The probe may be radiolabeled, labeled with a fluorescent material, a biotinylated nucleotide, or the like. Procedures for the preparation and labeling of nucleotide probes are well known in the art.

In situ hybridization of nucleotide probes to tissue sections is performed using standard methods, as described by, e.g., Baldino, et al., *Methods in Enzymol.,* 1989, vol. 168, p. 761–77; Emson, et al., *Methods in Enzymol.,* 1989, vol. 168, p. 753–61; Harper, et al., *Methods in Enzymol.,* 1987, vol. 151, p. 539–51; Angerer, et al., *Methods in Enzymol.,* 1987, vol. 152, p. 649–61; Wilcox, et al., *Methods in Enzymol.,* 1986, vol. 124, p. 510–33, incorporated herein by reference, using nucleotide probes described above. One preferred method for detecting mRNA associated with expression of the cross-reactive protein is in situ hybridization to tissue sections taken from tumors. Detection of hybridization by a probe having a nucleotide sequence corresponding to the amino acid sequence of NF-X1 in the cells indicates expression by that cell of mRNA corresponding to a protein cross-reactive with the NFX.1 gene product. Tissue sections are prepared as for immunohisto-chemistry.

Alternatively, extracts of RNA from tissue samples can be analyzed for the presence of sequences encoding the proteins of this invention. The diagnostic test employing a nucleotide probe will employ a biological sample from an individual. Nucleic acids are recovered from the sample employing standard techniques well known to those skilled in the art. The nucleic acid then is incubated with the probe and hybridization is thereafter detected. The presence of a nucleic acid whose sequence corresponds to that of the probe is preferably detected by Northern blot, or slot/dot blot. Using Northern blotting or dot hybridization, purified RNA samples of known concentration and integrity can be hybridized with labeled NF-X1 probes. For each sample, the signal which is obtained can be compared radiometrically to the signal obtained when the same sample is hybridized to a labelled probe for a constitutively expressed gene whose expression does not vary from cell to cell or sample to sample. Comparison of the ratios between different samples permits estimation of the differences in NFX.1 levels.

Alternatively, a nucleic acid whose sequence corresponds to the sequence of NF-X1 may be detected in the RNA extract of tumor tissue by nucleic acid amplification, using primers corresponding to the nucleic acid sequence of NF-X1, (see, e.g., methods reviewed in Van Brunt, *BioTechnology,.*8:291–294, 1990). Similar primers can be used to amplify genomic DNA sequences encoding NF-X1. The preferred method of amplification uses the polymerase chain reaction (PCR). Primers can be constructed corresponding to unique portions of the nucleic acid sequence of NF-X1, determined as described above for nucleic acid probes. Using these primers, RNA or DNA in a nucleic acid extract of tumor tissue will be amplified by PCR only if it contains the unique NF-X1 sequences.

The level of NFX.1 mRNA expression can be estimated by quantitative polymerase chain reaction. Using primers whose sequences correspond to the NFX.1 nucleotide sequence, cDNA can be synthesized initially using reverse transcriptase, then the resultant cDNA amplified according to the polymerase chain reaction. The reaction is run under conditions and terminated so as to produce amounts of amplified products in proportion to the amount of mRNA originally present in the sample. The amount of product can be quantitated by ethidium fluorescence in comparison to known standards following electrophoresis, or by dot hybridization with labeled probes. Expression of constitutively expressed genes can be measured as a control, permitting standardized comparison of results, such as with the previously described hybridization reactions. Treatment of samples with ribonuclease A or other RNAses in control samples prior to amplification verifies that the signal is derived solely from RNA.

Diagnostic Use of the NF-X1 Polypeptide and cDNA, and Genomic Clones Encoding It Autoimmune diseases result from both genetic and environmental factors. The genetic component of these diseases appears to be accounted for by multiple genes which segregate independently and which are required in certain combinations to make a particular individual genetically predisposed to develop these diseases. Much of genetic susceptibility is associated with particular alleles of either class I or class II MHC genes. Candidate genes for the other independently segregating genes include transcription factors which regulate the expression of these molecules.

Multiple autoimmune diseases exhibit aberrant expression of class II MHC molecules at the sites of autoimmune attack. Since autoimmune disease is associated with the inappropriate expression of class II MHC genes, mutations in a protein whose role is to down-regulate the expression of these molecules may account for a non-MHC encoded susceptibility gene. Alterations in expression or structure of the NFX.1 gene may directly participate in the genesis of these diseases. Nucleic acid reagents or short oligonucleotides derived from the NFX.1 sequence will therefore be of diagnostic utility in discovering the identity of patients that may be predisposed to develop autoimmune diseases.

As a candidate susceptibility gene for autoimmune diseases, and other diseases which might result from inappropriate expression of class II MHC genes, the cDNA and genomic clones or oligonucleotide primers derived from the sequence, may be used to screen genomic DNA samples from individuals that are suspected to be genetically predisposed to develop these diseases. Mutations or particular alleles of the NFX.1 gene may be detected by assays based upon nucleic acid hybridization or polymerase chain reaction. Assays based on the sequences provided by this invention can be used in epidemiologic studies to establish whether certain alleles or mutations in the NFX.1 gene are associated with the development of particular autoimmune or immune-initiated disorders.

We have also recently determined the NFX.1 gene and two related genes or pseudogenes are located in specific regions of human chromosome9. The nucleic acid reagents described above may therefore be used as markers for diseases that are located close to the NFX.1 gene. An example of such a disease is the neurodegenerative disorder Freidrich's Ataxia. Assays based on NFX.1 as a marker on chromosome 9 will not depend on whether NFX.1 has a direct role in this disease or is simply a useful marker for the disease.

Therapy using NFX.1

Due to the central and early role of class II MHC molecules in the immune response, a biological reagent which can repress the expression of these genes is valuable as the basis for novel approaches toward the treatment of immunologic diseases as well as in the promotion of graft survival. Mammalian expression vectors or small molecules derived from the NFX.1 amino acid sequence may have therapeutic value in a broad range of immunologic diseases. The inappropriate expression of these molecules may either initiate or exacerbate autoimmune diseases. A natural protein which, when overexpressed, can repress expression of these molecules may therefore form the basis of novel therapeutics that contribute to the prevention or management of this class of diseases.

Due to the role of class II MHC molecules in the rejection of organ and tissue transplants, the mammalian expression vectors or related vectors may be useful in prolonging graft survival. Vectors which overexpress the NFX.1 protein may be transfected into isolated cells or profused into tissues or organs prior to transplantation using known transfection procedures. Examples from the prior art for the insertion of DNA into eucaryotic cells can be found in the U.S. Pat. No. 4,399,216 issued on Aug. 16, 1983 to Axel et al, incorporated herein by reference. An example from the prior art for insertion of expression vectors into isolated cells for genetic therapy can be found in U.S. Pat. No. 5,166,059 issued to Pastan et al. issued on Nov. 24, 1992, incorporated herein by reference. Specific target tissues for introduction of NFX.1 expression vectors include but are not restricted to bone marrow, heart, lung, liver, pancreas, and kidney. Preferably, cells or organs will be explanted in vitro and transformed by either DNA transfection or infection with highly transmissible (but defective) viral vectors, followed by selection of cells incorporating the expression vector.

We have also demonstrated that NFX.1 is also a potent repressor of the cytokine, interleukin-4. Overexpression of NFX.1 represses production of interleukin-4 from the T-lymphocyte cell line, Jurkat, to less than $\frac{1}{18}$ of normal levels. Due to the critical role of interleukin-4 in the production of immunoglobulin E and this cytokine's likely role in human asthma and allergy, all of the reagents described above would also be useful in the management of allergic diseases.

In one embodiment of this invention, a method is provided for repressing unwanted MHC class II or interleukin-4 expression, which comprises obtaining a DNA expression vector containing a cDNA sequence having the sequence of human NFX.1 MRNA which is operably linked to a promoter such that it will be constituitively expressed, and transforming the cells which express MHC class II or interleukin-4 with the DNA vector. The expression vector material is generally produced by culture of recombinant or transfected cells and formulated in a pharmacologically acceptable solution or suspension, which is usually a physiologically-compatible aqueous solution, or in coated tablets, tablets, capsules, suppositories, inhalation aerosols, or ampules, as described in the art, for example in U.S. Pat. No. 4,446,128, incorporated herein by reference.

The vector-containing composition is administered to a mammal in an amount sufficient to transfect a substantial portion of the target cells of the mammal. Administration may be any suitable route, including oral, rectal, intranasal or by intravesicular (e.g. bladder) instillation or injection where injection may be, for example, transdermal, subcutaneous, intramuscular or intravenous. Preferably, the expression vector is administered to the mammal so that the cells of the mammal which overexpress MHC class II molecules or interleukin-4 are preferentially transfected. Determination of the amount to be administered will involve consideration of infectivity of the vector, transfection efficiency in vitro, immune response of the patient, etc. A typical initial dose for administration would be 10–1000 micrograms when administered intravenously, intramuscularly, subcutaneously, intravesicularly, or in inhalation aerosol, 100 to 1000 micrograms by mouth, or $10^5$ to $10^{10}$ plaque forming units of a recombinant vector, although this amount may be adjusted by a clinician doing the administration as commonly occurs in the administration of other pharmacological agents. A single administration may usually be sufficient to produce a therapeutic effect, but multiple administrations may be necessary to assure continued response over a substantial period of time. Further description of suitable methods of formulation and administration according to this invention may be found in U.S. Pat. Nos. 4,592,002 and 4,920,209, incorporated herein by reference.

Modifications of the above-described modes for carrying out the invention that are obvious to persons of skill in medicine, immunology, hybridoma technology, pharmacology, and/or related fields are intended to be within the scope of this invention.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

EXAMPLES

In order to facilitate a more complete understanding of the invention, a number of Examples are provided below. However, the scope of the invention is not limited to specific embodiments disclosed in these Examples, which are for purposes of illustration only.

The following cell lines and growth conditions were used in the Examples: Raji and Jijoye cells are MHC class II positive EBV-transformed human B lymphoblastoid cell lines. Jurkat is a class II negative human T cell line. All three lymphoid cell lines are maintained in RPMI 1640 supplemented with 10% heat-inactivated FCS, 20 mM Hepes, penicillin/streptomycin, 2 mM glutamine and 1 mM sodium pyruvate. HeLa cells were maintained in DMEM media. Transcription of the HLA-DRA gene and cell surface expression of the HLA-DR molecule is inducible by addition of recombinant gamma-interferon to these cells at a concentration of 100 U/ml for 24–48 hours.

Example 1
Isolation of cDNA clones encoding NF-X1

A number of overlapping complementary DNA clones encoding a newly identified human X1 box binding protein have been isolated by screening a Raji cell lambda gt11 expression library with a mixture of multimerized, radiolabelled, double-stranded oligonucleotides spanning the X boxes (and surrounding nucleotides) of the human class II MHC genes: HLA-DQB and -DPB (Driggers, et al., 1990, Proc. Natl. Acad. Sci. USA, 87:3743). Infection, plating, fusion protein induction and nitrocellulose filter lifts were performed as described in (Vinson, et al., 1988, Genes Dev., 1:806). The oligonucleotides used to probe the immobilized recombinant fusion proteins were:

HLA-DQB
X-[AAAATCTGCCCAGAGACAGATGAGGTCCTT] (SEQ ID NO:8) and

HLA-DPB
X-[ACTTTCTGCCTAGTGAGCAATGACTCATAC] (SEQ ID NO:9).

A HLA-DRA S box probe-[TGTGTCCTGGACCCTTTGCAAGA] (SEQ ID NO:10) was also included in the screens. Double-stranded oligonucleotides were end-labeled with [g-$^{32}$P]ATP using T4 polynucleotide kinase and subsequently concatenated with DNA ligase. Ligation efficiency was monitored by gel electrophoresis. Oligonucleotides were synthesized on an Applied Biosystems 391 DNA Synthesizer.

Figure 6:
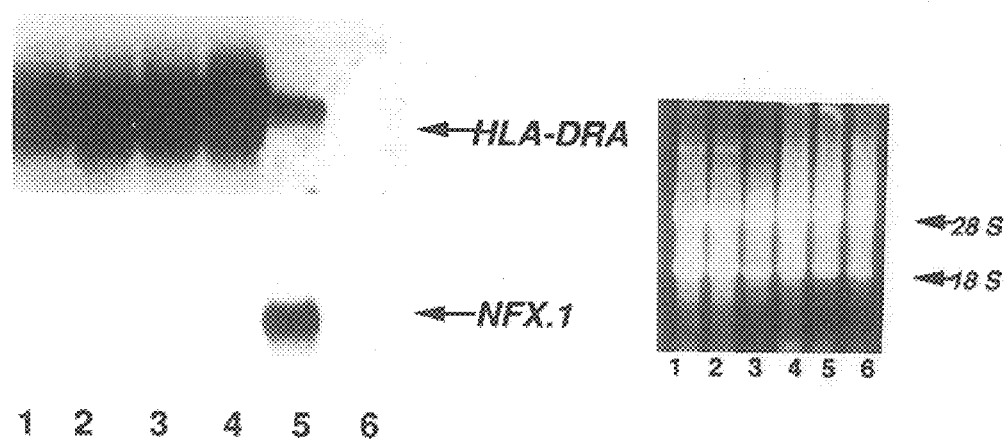
FIG. 6 shows a Northern blot analysis of HeLa cells probed with either a DRA specific or NFX.1 specific radiolabeled probe, showing that NFX.1 RNA is overexpressed late after incubation with interferon-gamma and this coincides with reduction in HLA-DRA mRNA.

Potential positive clones were subjected to secondary and tertiary screens. Insert cDNAs were then subcloned into pBluescript cloning/sequencing vectors and restriction maps generated. Through restriction mapping and dideoxy sequence analysis, six overlapping cDNAs have been found to encode the same DNA-binding protein, designated NF-X1. The restriction map and the sizes of the overlapping clones is shown in FIG. 1. Six overlapping cDNA inserts of bacteriophage clones encoding portions of a newly identified MHC class II X1-box binding protein, NF-X1, are shown. One of these clones: clone-16, encodes a full length (or nearly full length) copy of the NF-X1 mRNA as estimated by Northern blot analysis (FIG. 6 and data not shown). Bacteriophage clone-16, contains an insert of 4,053 nucleotides which encompasses all of the other cDNA inserts. A restriction map of the clone-16 EcoRI cDNA insert is shown. The MRNA contains a long open reading frame of 1104 amino acids with a short 5' untranslated region and a 741 base 3'-UT. Clone-16 contains a poly(A) tail.

Bidirectional exonuclease deletions of the full-length clone-16 insert were generated and both strands sequenced by the dideoxy method. A few regions that were between deletions oligonucleotides. The using complementary oligonucleotides. The complete nucleotide sequence of the clone-16 bacteriophage insert has been determined by 1) sequencing exonuclease generated truncations of the insert subcloned into the pBluescript vector (Stratagene), and 2) using oligonucleotide primers complementary to various locations within the cDNA to derive additional sequence information. Each portion of the cDNA has been sequenced multiple times and on both strands.

Clone-16 extends 4,053 nucleotides beyond a short 5' untranslated region, including a 3,312-base largest open reading frame, and 741 bases 3' of the termination codon. This clone contains the entire 3' untranslated region and contains a poly(A) tail. We have identified two other types of clones that contain shorter 3' untranslated regions followed by long poly(A) tails which presumably result from distinct poly(A) addition sites. The complete nucleotide sequence of an mRNA containing the first polyadenylation site is shown in FIG. 2A.

Example 2
Primary structure analysis of NF-X1

The complete deduced amino acid sequence of the largest open reading frame of the NFX.1 MRNA is shown in FIG. 2A from the first in-frame methionine to the most ORF-proximal polyadenylation site. No other significant open reading frames are detected in either strand, and in vitro transcription/translation of NF-X1 cDNA fragments produce polypeptides of molecular masses in agreement with this open reading frame. Two additional polyadenylation sites are also observed in additional clones (data not shown). The single large open reading frame encodes a polypeptide of 1104 amino acids. The estimated Mrs of the polypeptide is 121,440.

Figure 2B:
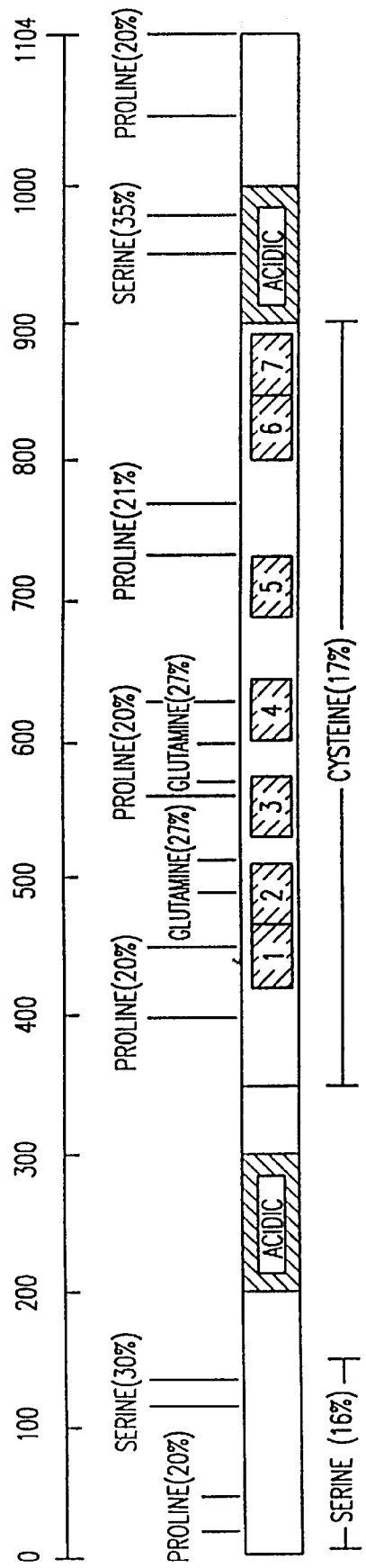

The entire amino acid sequence was subdivided into 22 fragments of 50 residues (with the final fragment containing 54 residues) and analyzed using the Gene Works software program (Intelligenetics, Mountainview, Calif.). Primary structural analysis of NF-X1 indicates that the protein has a general symmetrical organization. Graphic representation of the primary structure in FIG. 2B shows the general symmetrical organization of the protein, with a 550-residue central region rich in cysteine (17%). Seven repeats of approximately 40 residues in length are indicated within the cysteine-rich domain. Proline, serine and glutamine-rich regions are also indicated between lines placed above the representation of the primary sequence. Two acidic regions are found at the N and C-termini.

Figure 2C:
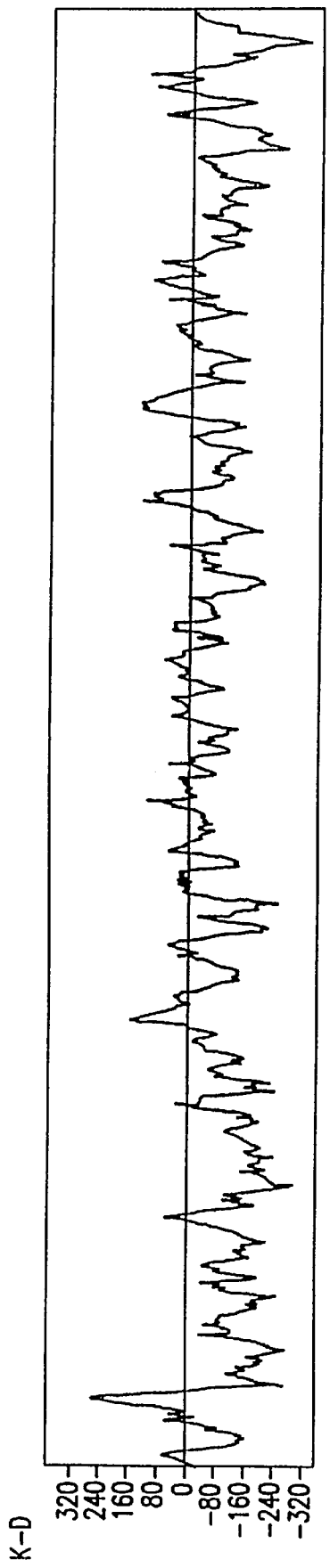
Figure 2E:
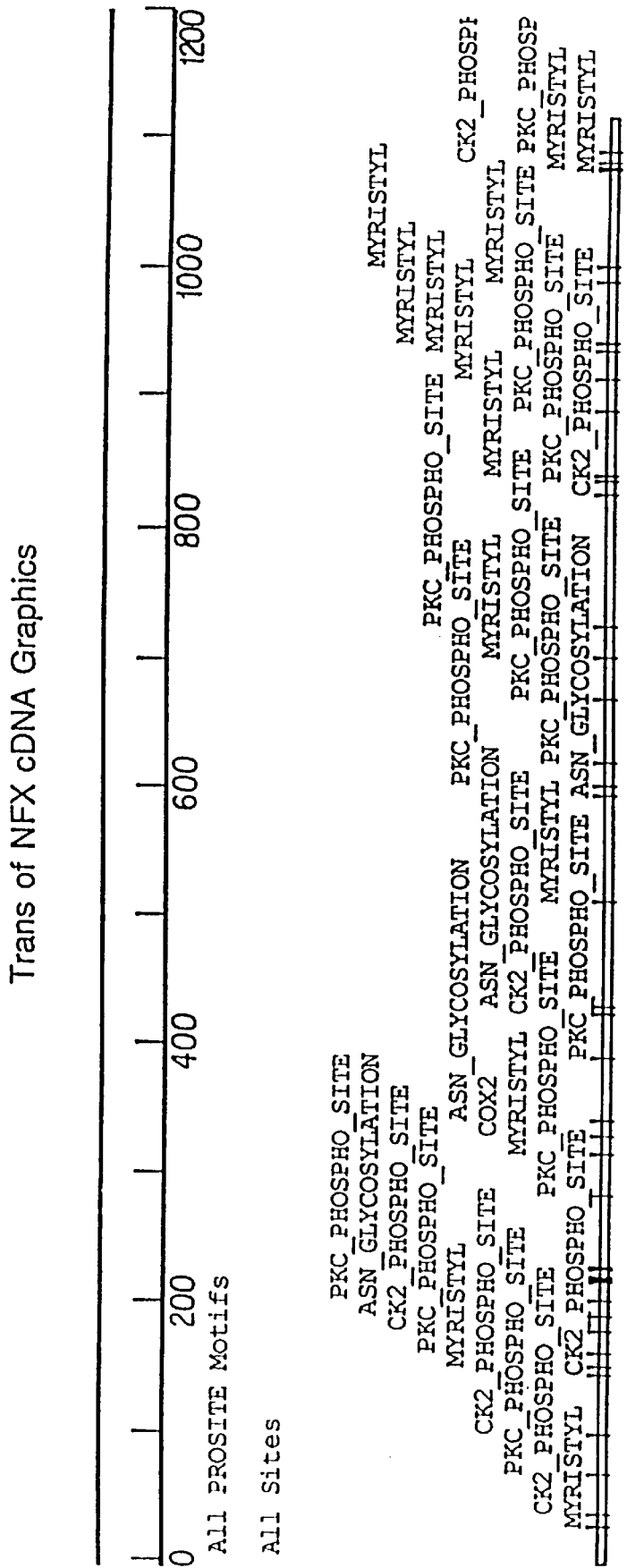

The polypeptide has four potential sites for N-linked glycosylation and fifty-two potential cAMP, CK2 and PKC phosphorylation and myristylation sites scattered throughout the polypeptide. The location of these sites is depicted in FIG. 2E. This high density of potential post-translational modification sites suggests that these modifications may play an important role in regulating the function of NF-X1.

Hydropathy analysis using the algorithm of Kyte and Doolittle (Kyte, et al., 1982,J. Mol. Biol., 157:105) indicates that the polypeptide is generally hydrophobic with the exception of the central domain (residues 430 to 680) which is less hydrophobic (see FIG. 2C). Seven repeated domains with the general consensus sequence: CxxxCxxxLxCGx1-5HxCxxxCHxGxC(SEQ ID NOS:1 & 2) are found in this region and these repeats are aligned in FIG. 2D. The repeat motif was detected by screening for internal homology using the FASTP program and the Gene Works software. The consensus sequence was derived by aligning the repeat motifs. The numbers to the left of the polypeptides indicate the amino acid positions included in each repeat, and the numbers below the consensus indicate the number of repeats that contain the consensus amino acid. The repeated domains are roughly 40 residues in length.

The homology is greatest in the central portion of the repeat and decreases away from the center. However, several cysteine residues within the repeats appear to be conserved regardless of their distance from the central homologous region. It is possible that these conserved cysteines serve as a framework for the structure of the repeating domain via disulfide linkages, metal complexes or an alternative mechanism.

The existence of a cysteine-rich domain raises the possibility that this region might mediate sequence-specific binding via the formation of zinc finger(s). However, an exhaustive analysis for prototypical zinc-finger motifs does not reveal any typical zinc finger motifs of the C2C2 or C2H2 types. Although several cysteine and histidine residues do exist in the NF-X1 repeats, the distances between them and in potential linking regions are non-standard (Desjarlais, et al., 1993, *Proc. Natl. Acad. Sci. USA*, 90:2256). The repeated motif is itself most similar to but distinct from two previously described families of metal binding proteins: the LIM domain and the RING finger families, and is therefore likely to represent a novel metal binding domain (Freemont, et al., 1991, *Cell*, 60:483; Freyd, et al., 1990, *Nature*, 344:876). The motif is highly significant since only seven proteins in the protein data base contain stretches that are similar to the described motif, with the probability of detection being approximately $1.5 \times 10^{-5}$. All of the proteins that contain related motifs [e.g. RAG-1, *S. cervisiae* RAD18, Herpes Simplex IE110, the ret oncogene, the *C. elegans* developmental gene lin-11, and the insulin gene enhancer binding protein Isl-1] are thought to interact with DNA, although they are involved in the distinct enzymatic processes of recombination, repair and transcriptional regulation. Recombinant NF-X1 prepared as described herein may be used to show what sort of structures form in this region and how they might mediate sequence-specific binding.

The NF-X1 polypeptide contains several other features that are characteristic of transcription factors. Two acidic regions (between residues 200–300 and 900–1000) surround the cysteine-rich domain. Three regions rich in proline (>20%) and two regions rich in glutamine (27%) are located within the cysteine-rich domain. Two serine-rich regions (>30%) are located 100 residues from each terminus, and two proline-rich (>20%) segments are found at the termini of the polypeptide.

Example 3
Genomic organization and transcription of the NF-X 1 gene

High molecular weight DNA was isolated from murine splenocytes (lanes 1 and 2 of FIG. 3A) and from the human B-lymphoma cell line, Clone-13 (lanes 3 and 4) as previously described (Sambrook, et al., 1989). 20 ug of DNA was digested to completion with EcoRI (lanes 1 and 3) or BamHI (lanes 2 and 4) and resolved on a 1% agarose gel. DNA was transferred to Gene Screen Plus hybridization membranes and prehybridized, hybridized and washed according to the manufacturer's guidelines (DuPont-NEN). The hybridization probe was the EcoRI insert from the Clone-16 bacteriophage. The Southern blot was subsequently washed at high stringency and subjected to autoradiography. The positions of DNA markers of HindIII digested bacteriophage lambda DNA are indicated by arrows.

Figure 3A:
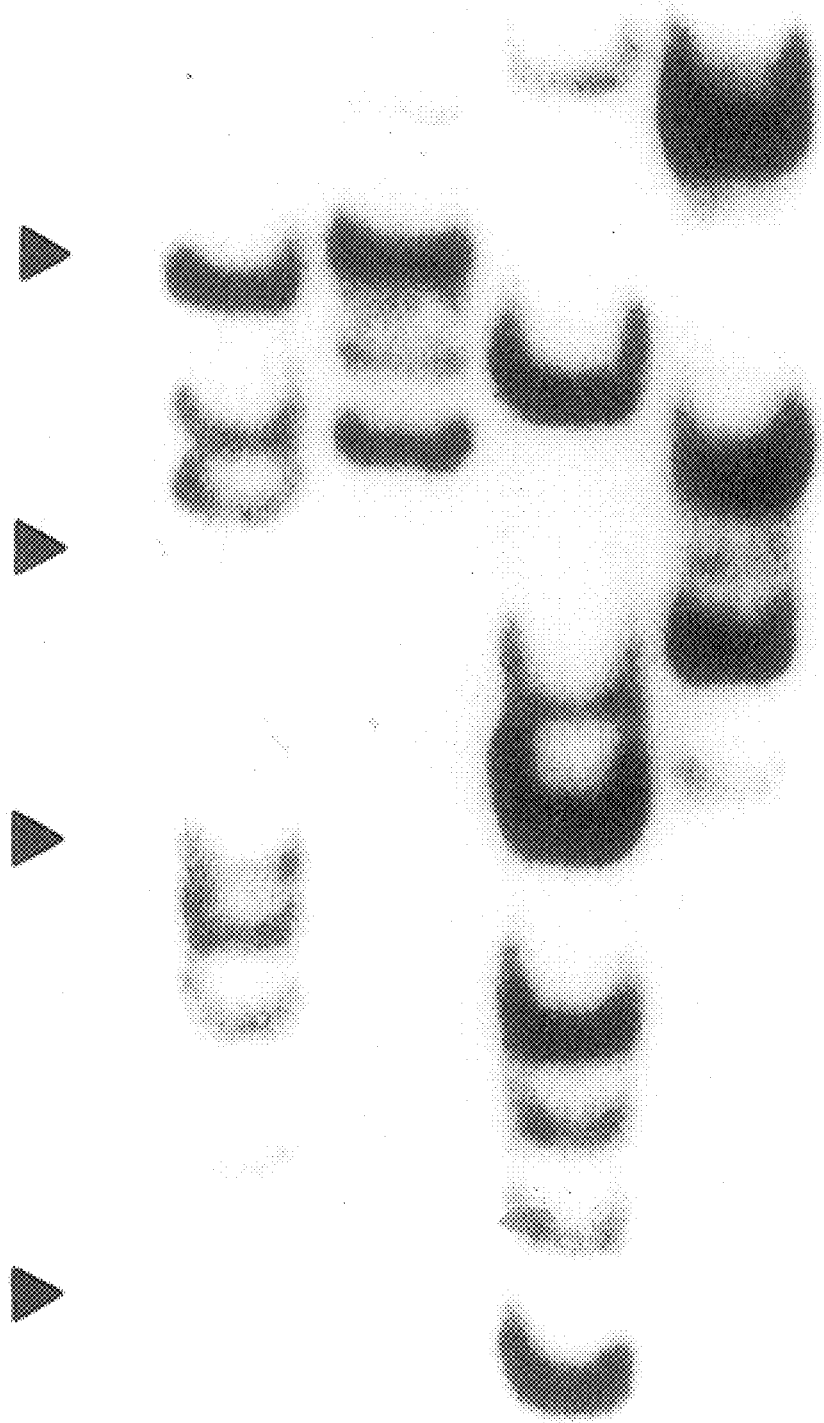
FIGS. 3A–C show the genomic organization and transcription of the NF-X1 gene. A) Genomic Southern blot probed with radiolabeled NF-X1 cDNA insert. B) RT-PCR analysis of total RNA isolated from Jijoye, Jurkat and RJ2.2.5. C) RNase protection analysis of total RNA isolated from class II MHC positive and negative cell lines.

Southern blot analysis of human genomic DNA digested with multiple restriction enzymes (using the clone-16 cDNA insert as a probe) reveals multiple bands ranging in size from approximately 4 to greater than 23 kilobases in length (FIG. 3A). As the sum of these fragments greatly exceeds the total length of the NF-X1 mRNA, we conclude that the NF-X1 gene is interrupted by introns of considerable size or that a related gene or genes (or pseudogenes) exists within the human genome. Southern blot analysis of genomic DNA isolated from mouse, Drosophila and yeast cells detects homologous sequences in each organism and indicates that the NF-X1 gene (or a related gene) is evolutionarily conserved (data not shown).

Northern blotting was also performed using the same membranes according to manufacturer's protocols using the same DNA probe. The HLA-DRA specific probe is as previously described (Ono, et al., *J. Exp. Med.*, 1991). RNA was isolated using the guanidium thiocyanate procedure (Chirgwin, et al., 1979, *Biochemistry*, 18:5294). 20 µg of total cellular RNA was separated after denaturation on an agarose/formaldehyde gel, transferred to hybridization membrane and probed with the NF-X1 cDNA. The Northern blots were washed at high stringency and subjected to autoradiography. Northern blot analysis of total RNA isolated from B and T cell lines detects an mRNA of approximately 4 kilobases in size which is expressed at very low levels (data not shown).

Figure 3B:
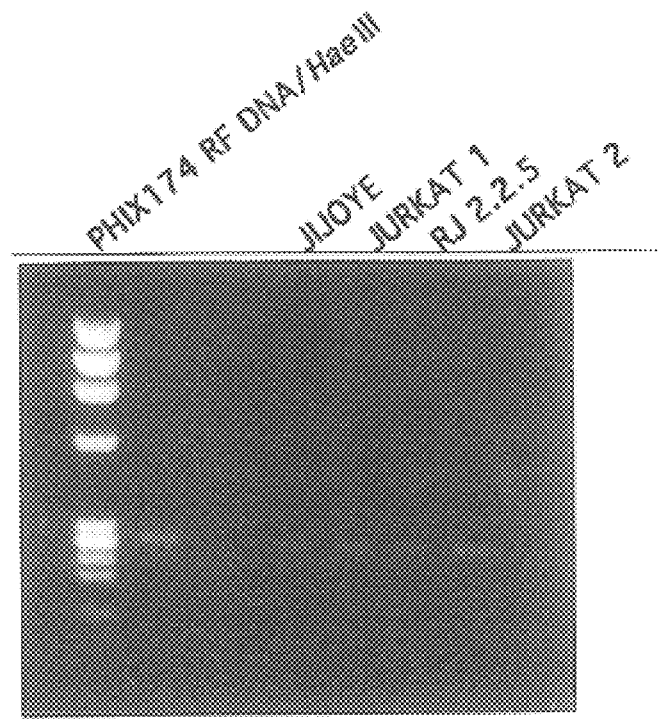

Since the NF-X1 mRNA is present in low abundance, both an RT-PCR and an RNase protection assay have been used for its detection and quantitation. cDNA synthesized from total RNA extracted from the class II positive B lymphoblastoid cell line Jijoye, and the class II negative cell lines Jurkat (T cell) and RJ2.2.5 (mutant B-LCL), has been used as substrates for polymerase chain reaction using two antiparallel oligonucleotides derived from the NF-X1 cDNA sequence. RT-7PCR was performed on samples of HeLa, Jurkat and Jijoye total RNA isolated using the GIT/CsCl procedure. cDNA synthesis was performed with 10 ug of total RNA in 50 mM Tris-HCl pH 8.3, 10 mM MgCl2, 100 mM KCl, 10 mM DTT and 500 µmole of each dNTP, 25 pmol 3' PCR primer, 7 U AMV-reverse transcriptase and 1 µl of RNAsin (Promega). The total reaction volume was 11 µl. After incubation at 37° C. for 1 hour, 5 µl of cDNA reaction mixture was used for amplification via polymerase chain reaction using internal NF-X1 antiparallel oligonucleotide primers. This non-quantitative RT-PCR detects NF-X1 mRNA in each cell line, regardless of class II phenotype (FIG. 3B). Lane assignments are: 1) Lambda Hind III+ PhiX174/Hae III, 2) positive control, 3) negative control (no template), 4) Jijoye template, 5) Jurkat template, and 6) RJ.2.2.5 template.

Figure 3C:
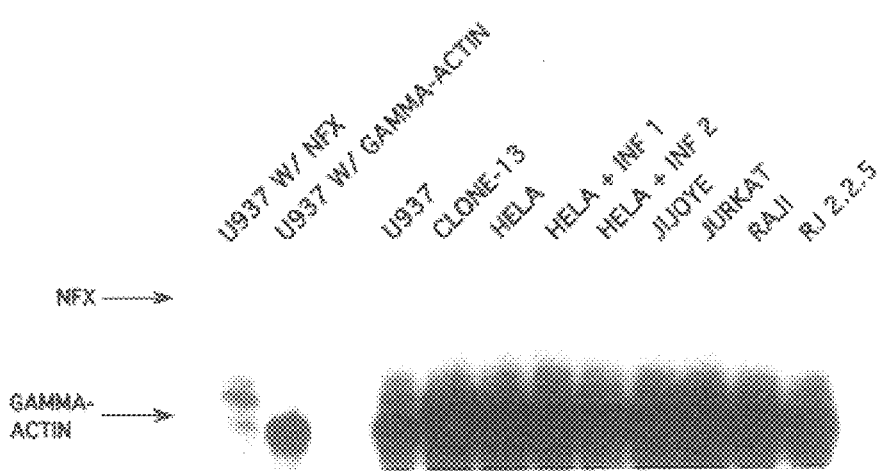

A larger panel of RNAs extracted from several class II positive and negative cell lines have also been analyzed for the presence of NF-X1 mRNA using a sensitive and quantitative RNase protection assay (FIG. 3C). Total RNA was isolated from class II MHC positive and negative cell lines. The RNAs utilized in the lanes labeled HELA+INF were extracted from HeLa cells incubated for 24 hours with 250 U/ml interferon-g. For RNase protection analysis an antisense probe for the human gamma-actin gene was synthesized by linearizing the plasmid SP6-gamma-actin (Zinn, et al., 1983, *Cell*, 34:865) with HinfII (New England Biolabs) followed by transcription in vitro using SP6 RNA polymerase (Gibco-Bethesda Research Laboratories) and 32P CTP (800 Ci/mmol; DuPont/NEN). 3.2 kilobases of the NF-X1 cDNA was subcloned into pbluescript to generate pBSClone-16. The antisense probe for NF-X1 was prepared by first linearizing the pBSClone-16 plasmid with AatII and transcribed using T7 RNA polymerase. 25 μg of each total RNA preparation was lyophilized and hybridized at 45° C. with 500,000 cpm of each labeled riboprobe. Hybrids were digested for 30 minutes at 30° C. with RNAse One (Promega) as recommended by the manufacturer. These analyses demonstrate that the NF-X1 mRNA is ubiquitously expressed in all cell lines tested and is present at an abundance approximately fifty-fold lower than an internal gamma-actin control.

Example 4

NF-X1 encodes a promiscuous X1 box binding protein

Secondary and tertiary screens of bacteriophage clones isolated in this screening included an initial assessment of sequence-specificity of encoded DNA-binding proteins by incubation of sections of nitrocellulose filter "lifts" with multiple radiolabeled recognition site probes. These analyses indicated that the NF-X1 protein interacts with both the DQB and DPB extended X box proteins but not with the HLA-DRA S-box recognition site (data not shown). To allow further analysis of binding specificity, bacteriophage lysogens were constructed from the initial clone-16 bacteriophage using the method of Singh (Singh, et al., 1988, Cell, 52:415). NF-X1 was produced either as a lysogen as described in the text, or from the T7 expression system (Studier, et al., 1986, J. Mol. Biol., 189:113). Protein was partially purified as previously described (Gaul, et al., 1987, Cell, 50:639) and dialyzed against 50 mM Tris (pH 7.9), 0.5M NaCl, 10% glycerol and 1 mM PMSF. The binding specificity of isolated NF-X1 fusion protein induced after 1 hour incubation in 10 mM isoprylthio-beta-D-galactoside has been assessed by electrophoretic mobility shift analysis (FIG. 4A). Gel mobility shift assays were performed by incubating bacterially produced NF-X1 with end-labeled probes for 30 minutes at room temperature in binding buffer consisting of 13 mM Tris (pH7.9), 60 mM KCl, 12.5 mM NaCl, 12% glycerol, and 75 ug/ml poly dIdC. The binding reactions were then resolved on low ionic strength 5% nondenaturing polyacrylamide gels and electrophoresed at 10V/cm at room temperature (Strauss, et al., 1984, Cell, 3:889). Recombinant NF-X1 forms a specific complex with the double-stranded, DRA X1 box oligonucleotide [5'CCCTTCCCCTAGCAACAGATG-3'] (SEQ ID NO:3) which is competed for by 100-fold excess cold, double-stranded oligonucleotides containing the analogous regions from the HLA-DRB, -DPA, -DPB, -DQA and -DQB promoters but not by HLA-DRA Y-box [5'AAATATTTTTCTGATTGGCCAAAGAGT3'] (SEQ ID NO:11), S-box [5'TGTGTCCTGGACCCTTTGCAAGA3'] (SEQ ID NO:10), SP1 [5'ATTCGATCGGGGCGGGGCGAGC3'] (SEQ ID NO:12) or the interferon-beta gene positive-regulatory domain II (PRDII) element [5'GTGGGAAATTCCGTGGGAAATTCCG3'] (SEQ ID NO:13). Recombinant NF-X1 binds to a radiolabeled, double-stranded oligonucleotide containing only the X1 box of the HLA-DRA gene promoter and 7 nucleotides upstream of the element [5'CCCTTCCCCTAGCAACAGATG3'] (SEQ ID NO:3). The shift is abolished by adding 100-fold excess unlabeled competitor oligonucleotides containing the analogous regions of the other human class II MHC gene promoters: HLA-DRB, -DPA, -DPB, -DQA and -DQB. Addition of 100-fold excess unlabeled competitor oligonucleotide representing other elements in the HLA-DRA promoter [the Y-box and the S-box] or elements found in other promoters [the SP1 motif and the PRDII element of the human interferon-beta gene promoter] does not influence the interaction of NF-X1 with its cognate recognition sequence. These data indicate that NF-X1 interacts sequence-specifically with all human class II MHC X1 boxes.

Example 5

Delineation of the DNA-binding domain of NF-X1

Figure 4B:
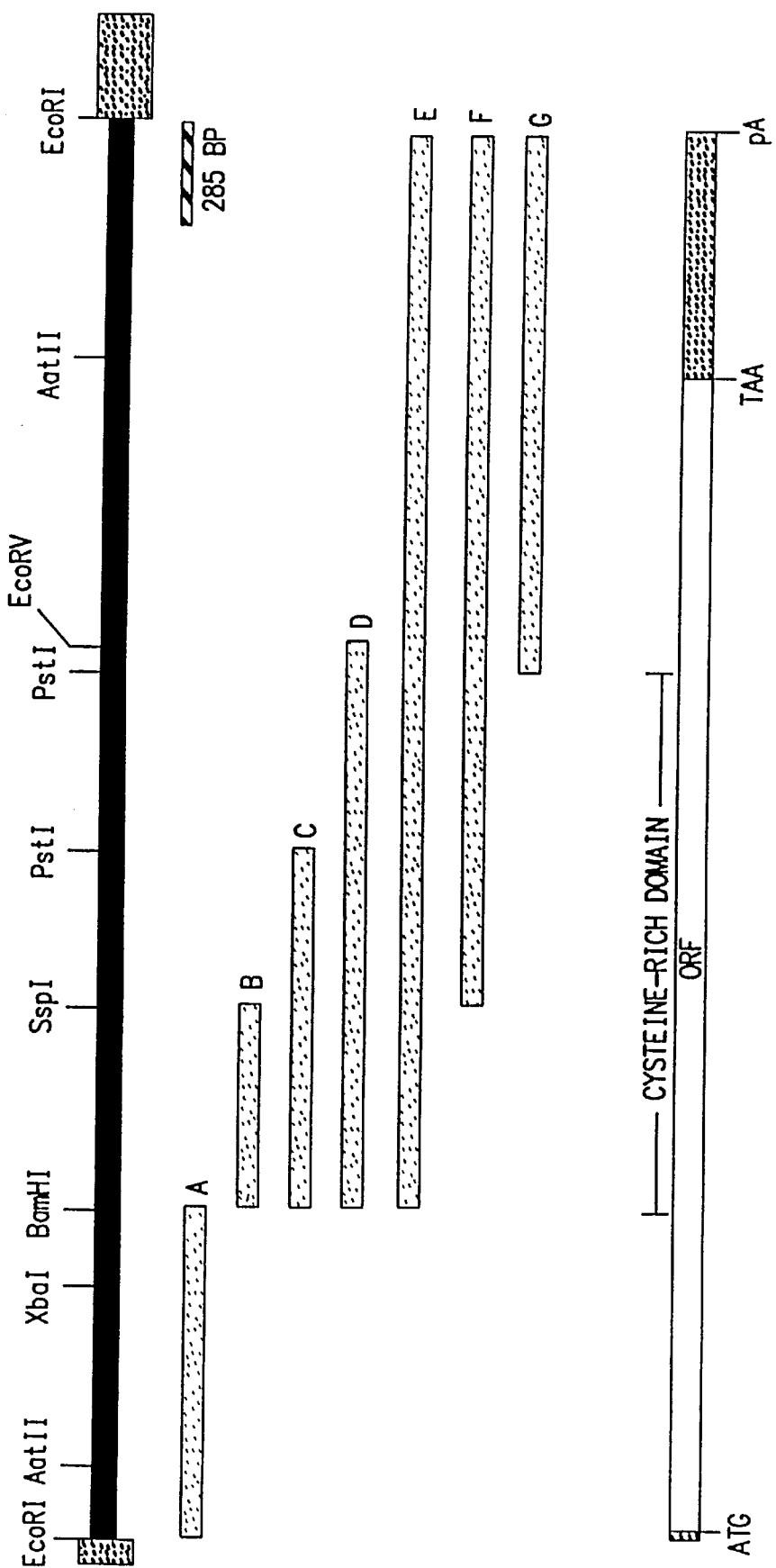

Using the strategy of Keller and Maniatis (Keller, et al., 1992, Mol. Cell. Biol., 12:1940), an initial definition of the NF-X1 DNA-binding domain has been accomplished (FIG. 4B). Truncated forms of the NF-X1 CDNA were created by polymerase chain reaction and ligated into EcoRI-cleaved, phosphatased lambda gt11 DNA (Singh, et al., 1989, BioTechniques, 7:252). In brief, truncated forms of the NF-X1 cDNA were generated using the indicated restriction endonucleases, inserted into the pRSET series of bacterial expression vectors as described, and subsequently subcloned into the λgt11 bacteriophage and LNCX mammalian expression vectors. Truncated NF-X1 cDNA fragments were first subcloned into appropriate pRSET vectors (Invitrogen) to place a methionine residue N-terminal and in frame with the fragment. NF-X1.A was subcloned into the pRSET.C vector with a N-terminal EcoRI site, NF-X1.(B–E) were subcloned into pRSET.B with a N-terminal BamHI site, NF-X1.F was subcloned into pRSET.C with a N-terminal SspI site, and NF-X1.G was subcloned ino pRSET.A with a N-terminal PstI site. Polymerase chain reaction was used to amplify the resulting expression casettes and to insert terminal EcoRI recognition sites where appropriate. These products were purified by binding to glass beads and ligated to λgt11 bacteriophage arms (Stratagene). The recombinant bacteriophage DNA was then packaged in high-efficiency phage packaging extract (Stratagene). The titer and frequency of recombination of the recombinant phage was determined by plating on Y1088 E. coli with IPTG and Xgal included in the plates. The ability of each subclone to generate the expected polypeptide was assessed by in vitro transcription/ translation of linearized templates and analysis of translation products on SDS/polyacrylamide gels (data not shown). The relative positions of each fragment relative to the open reading frame are indicated.

Figure 4C:
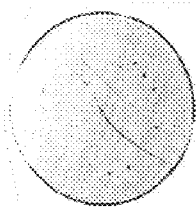
Figure 4C:
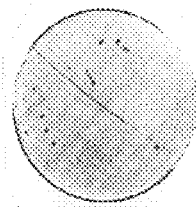
Figure 4C:
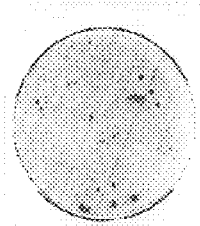
Figure 4C:
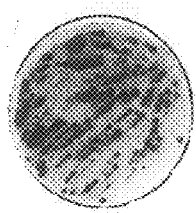
Figure 4C:
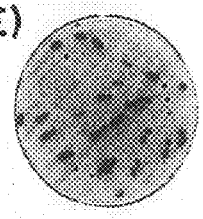
Figure 4C:
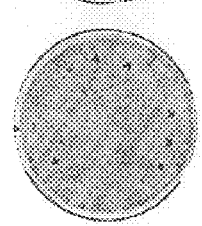
Figure 4C:
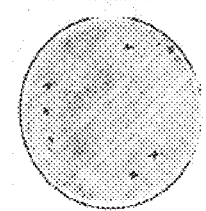

Several recombinant plaques were isolated for each construction and dideoxy sequence analysis of minipreparations of phage DNA was performed to identify bacteriophage particles harboring the NF-X1 truncations in frame with the amino-terminal portion of beta-galactosidase. The ligation reaction was then packaged (Gigapack Gold; Stratagene) and plated on Y1090 bacteria (Young, 1983, Proc. Natl. Acad. Sci. USA, 80:1194). These phage were then plated on Y1090 bacteria, the various truncated NF-X1 fusion proteins induced, and assessed for their ability to bind radiolabeled DRA-X1 box oligonucleotides using the filter binding assay. Individual plaques were purified and assessed for insert orientation and binding ability in filter binding assays. After plaque lifting, filters were subjected to stepwise denaturation-renaturation and screened with multimerized radiolabeled probes as previously described (Driggers, et al., 1990). The binding buffer consisted of: 12 mM Tris (7.9), 40 mM KCl,0.12 mM EDTA, 30 uM ZnSO4, and 400 uM b-mercaptoethanol. Bovine serum albumin (fraction V) was used in place of dried non fat milk as a blocking agent. The binding and washing reactions were performed at 4° C. Autoradiographs were exposed overnight with intensifying screens. The data presented in FIG. 4C show that the entire cysteine-rich region spanning amino acids 420 to 900 is necessary and sufficient to mediate interaction with the HLA-DRA X1 box. Recombinant NF-X1 fusion proteins encoded by lgt11 phages D and E retain X1-box binding activity.

Example 6
NF-X1 encodes a repressor of HLA-DRA transcription

NF-X1 encodes a repressor of HLA-DRA transcription and requires the cysteine-rich DNA-binding domain for regulatory function. The regulatory function and effector domain(s) of NF-X1 have been investigated using mammalian expression vectors encoding the wild type and six truncated NF-X1 polypeptides. The six truncated NF-X1 forms described in FIG. 4B were generated by first subcloning the indicated NF-X1 restriction fragments in frame with the N-terminal peptide of the pRSET A,B,C series of expression vectors (Invitrogen) to provide an N-terminal methionine residue to each NF-X1 subfragment. The resulting "expression cassettes" were then subcloned utilizing PCR methods into the retroviral vector pLNCX (shown in FIG. 5A) to generate a series of mammalian expression vectors for cotransfection studies in mammalian cells (Hantzopoulos, et al., 1989, Proc. Natl. Acad. Sci. USA, 86:3519). Each expression cassette was tested for its ability to direct the synthesis of the desired NF-X1 polypeptide by in vitro transcription and translation from linearized pRSET derivatives (not shown).

The regulatory function of NF-X1 has been assessed by cotransfection experiments where mammalian expression vectors encoding the wild-type and truncation derivatives of NF-X1 have been cotransfected with the HLA-DRA reporter construct DRA300CAT into a series of class II positive, class II negative and gamma-interferon inducible cell lines (Tsang, et al., Proc. Natl. Acad. Sci. USA, 85:8598). Transfections were either performed using the DEAE dextran method, as previously described in (Ono, et al., J. Exp. Med., 1991), or using the lipofectamine reagent (Bethesda Research Laboratories) according to manufacturer's specifications. Typical transfections included varying amounts of effector plasmid (1 to 15 µg) and 1 to 5 µg of reporter construct and 5 µg of tkHGH transfection control plasmid. 48 hours post-transfection cells were harvested by centrifugation, washed twice, and extracts prepared by multiple cycles of freeze/thaw. CAT assays were performed as previously described (Ono, et al., J. Exp. Med., 1991; Ono, et al., 1991, Proc. Natl. Acad. Sci. USA, 88:4304; Ono, et al., 1991, Proc. Natl. Acad. Sci. USA, 88:4309). Each transfection experiment was performed 5 times to calculate standard errors.

Figure 5B:
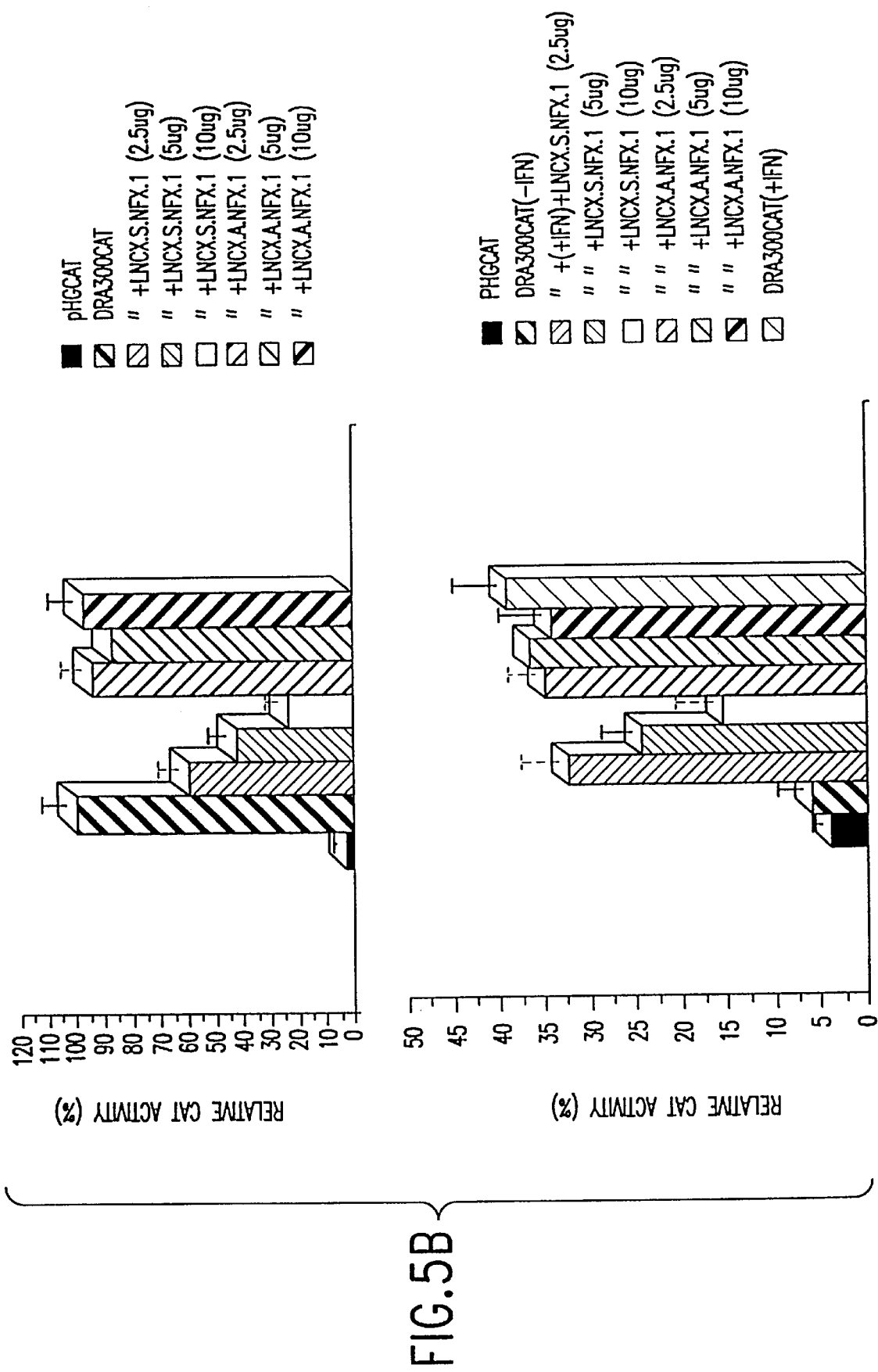

Histograms showing the CAT activity produced in the class II MHC positive cell line Raji and the class II inducible cell line HeLa after cotransfection with the HLA-DRA promoter reporter construct DRA300CAT and increasing amounts of the LNCX expression vectors containing the NF-X1 cDNA in either the sense or antisense orientations are shown in FIG. 5B. CAT activities are normalize to a cotransfected HGH expression vector as described (Ono, et al., J. Exp. Med., 1991). Wild-type NF-X1 has been found to encode a potent repressor of HLA-DRA transcription in the class II positive cell Raji (FIG. 5B). It also represses DRA transcription in interferon-gamma treated HeLa cells, but has no effect on DRA transcription in untreated HeLa cells and the class II negative T cell line Jurkat (FIG. 5B and data not shown). Overexpression of NF-X1 has no effect on transcription from reporter constructs that lack the X1 binding site such as a c-fos reporter construct, FC4, and RSVCAT (not shown).

Figure 5C:
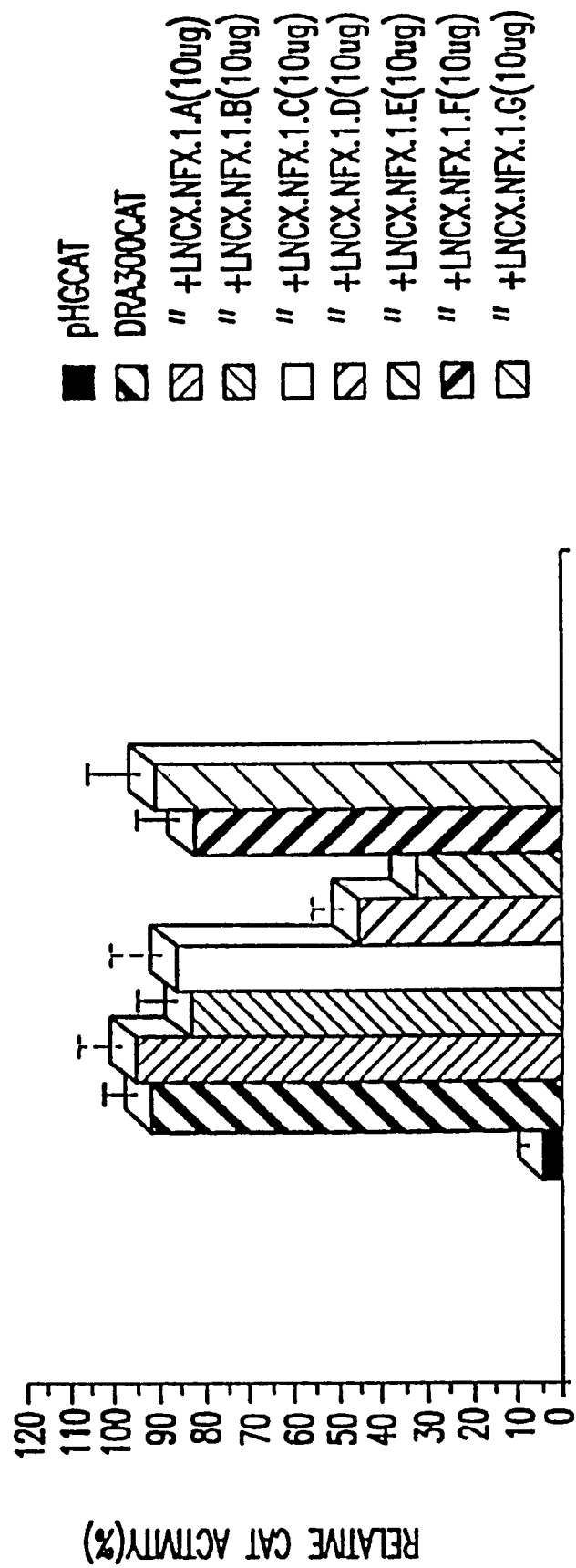

Transcriptional repression requires the DNA-binding domain of NF-X 1. Using the expression vectors encoding truncated NF-X1 forms, the cysteine-rich DNA binding domain has been shown to be necessary and sufficient to mediate this transcriptional repression. FIG. 5C contains histograms showing CAT activity in Raji cells after cotransfection with DRA300CAT and expression vectors containing the previously described subfragments of the NF-X1 cDNA. Only the LNCX.D and LNCX.E expression vectors mediate transcriptional repression from the DRA promoter. Other NF-X1 forms, lacking significant regions of the DNA-binding domain, cannot repress HLA-DRA transcription.

NFX.1 RNA is overexpressed late after incubation with interferon-gamma and this coincides with reduction in HLA-DRA mRNA. HeLa cells were incubated with 250 U/ml recombinant gamma-interferon for the indicated number of hours prior to isolation of total RNA. 20 µg of total RNA from each sample was resolved by electrophoresis through a formaldehyde agarose gel and was transferred to a Gene Screen hybridization membrane by capillary transfer. A photograph of the ethidium bromide stained gel is presented to show that equivalent amounts of RNA were loaded for each sample. The same membrane was then probed with either a DRA specific or NFX.1 specific radiolabeled probe, and the autoradiographs are presented. The DRA gene is strongly induced by interferon-gamma and the level of DRA transcript increases to a maximal level 24 hours postinduction. The level of DRA transcript is significantly reduced at 48 hours postinduction. The NFX.1 gene is expressed at very low levels as shown in FIG. 3B, but is overexpressed at 48 hours postinduction.

The NFX.1 mRNA is markedly induced late after incubation with interferon-gamma and this coincides with transcriptional attenuation of the HLA-DRA gene. Since artificial overexpression of the NFX.1 mRNA from retroviral constructs could repress transcription from the HLA-DRA promoter, a careful kinetic analysis of NFX.1 mRNA expression at several time points post-incubation with interferon-gamma was performed (FIG. 6). As is shown in FIG. 3B, NFX.1 mRNA expression is difficult to detect in RNA derived from uninduced HeLa cells, and from HeLa cells incubated for short periods of time with 100–200 U/ml recombinant gamma-interferon. In contrast, the NFX.1 transcript is expressed at high levels in RNA derived from HeLa cells incubated for 48 hours in the same concentration of gamma-interferon. This overexpression of NFX.1 mRNA coincides with a marked reduction in the steady state level of HLA-DRA transcript. The level of DRA transcript increases during the first 24 hours of incubation with interferon-gamma and decreases significantly by 48 hours postinduction (FIG. 6 and unpublished data). In view of the inhibitory effect of NFX.1 overexpression on HLA-DRA transcription (FIG. 5), these kinetic data strongly suggest that the NFX.1 protein functions in the postinduction turnoff of the HLA-DRA gene late after induction with interferon-gamma.

It will be understood that while the present invention has been described in conjunction with specific embodiments thereof, the foregoing description and examples are intended to illustrate, but not limit the scope of the invention. Other aspects, advantages and modifications will be apparent to those skilled in the art to which the invention pertains, and these aspects and modifications are contemplated within the scope of this invention, which is limited only by the appended claims.

Deposit

Plasmid Clone-16, prepared as described in Example 1, was deposited with the American Type Culture Collection, Rockville, Md., on Sep. 29, 1994, under ATCC Accession No. 75895. This deposit will be maintained under the terms of the Budapest Treaty on the International Recognition of the Deposit of Micro-organisms for purposes of patent procedure. This deposit is provided merely as convenience to those of skill in the art, and is not an admission that a deposit is required under 35 U.S.C. Section 112. The sequence of the polynucleotides contained in the deposited materials, as well as the amino acid sequence of the polypeptides encoded thereby, are incorporated herein by reference and are controlling in the event of any conflict with the description of sequences herein. A license may be required to make, use or sell the deposited materials, and no such license is hereby granted.

We claim:

1. A chimeric DNA molecule comprising a DNA sequence that encodes a polypeptide having a sequence corresponding to SEQ ID NO:5, the sequence of said polypeptide selected from the group consisting of SEQ ID NO:5, muteins of SEQ ID NO:5, truncations of SEQ ID NO:5, and fusion proteins containing them, wherein said polypeptide specifically binds to double stranded DNA having the sequence of SEQ ID NO:3.

2. The chimeric DNA molecule of claim 1, wherein said DNA sequence encoding said polypeptide is an intron-free DNA sequence.

3. A cell population transformed with the DNA molecule of claim 1, said population being substantially free of cells not transformed with said DNA molecule.

4. A composition comprising the chimeric DNA molecule of claim 1 and a pharmaceutically acceptable carrier.

5. A method of producing a polypeptide which contains at least about five copies of a cysteine rich sequence according to SEQ ID NO:1 coupled to a cysteine rich sequence according to SEQ ID NO:2 by a bridge peptide of from one to five amino acids, said polypeptide specifically binding to double stranded DNA having a sequence according to SEQ ID NO:3, comprising:

provifing a population of transformed cells of claim 3;

growing said population under conditions whereby said polypeptide is expressed; and recovering said polypeptide.

6. The method of claim 5 where said polypeptide is excreted by said cell.

7. A DNA molecule comprising an intron-free DNA sequence encoding the amino acid sequence of SEQ ID NO:5.

8. The DNA molecule according to claim 7, corresponding to SEQ ID NO:4.

9. The DNA molecule according to claim 7 comprising a DNA sequence encoding NF-X1 found in a plasmid deposited under ATCC Accession No. 75895.

10. A single stranded DNA molecule comprising at least 20 sequential nucleotides, wherein said sequential nucleotides comprise a subsequence found in SEQ ID NO:4 or a DNA sequence complementary thereto.

11. A method for determining the presence of a polynucleotide substantially homologous to a coding sequence for a polypeptide which contains at least about five copies of a cysteine rich sequence according to SEQ ID NO:1 coupled to a cysteine rich sequence according to SEQ ID NO:2 by a bridge peptide of from one to five amino acids, said polypeptide specifically binding to double stranded DNA having a sequence according to SEQ ID NO:3, comprising:

providing a sample suspected of comprising said polynucleotide;

incubating the sample with a nucleotide probe having a sequence complementary to the single stranded DNA of claim 1, under conditions where said probe will form hybrids with nucleic acids substantially homologous to said probe, detecting nucleic acid hybrids; and the presence of nucleic acid hybrids indicating the presence of said polynucleotide.

\* \* \* \* \*

```
                          SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
         (A) LENGTH: 12 amino acids
         (B) TYPE: amino acid
         (C) STRANDEDNESS: single
         (D) TOPOLOGY: linear (ii) MOLECULE TYPE: peptide (vi) ORIGINAL SOURCE:
         (A) ORGANISM: Homo sapiens (xi) SEQUENCE DESCRIPTION: SEQ ID NO:1:

Cys Xaa Xaa Xaa Cys Xaa Xaa Xaa Leu Xaa Cys Gly
1               5                   10

(2) INFORMATION FOR SEQ ID NO:2:

(i) SEQUENCE CHARACTERISTICS:
         (A) LENGTH: 12 amino acids
         (B) TYPE: amino acid
         (C) STRANDEDNESS: single
         (D) TOPOLOGY: linear (ii) MOLECULE TYPE: peptide (vi) ORIGINAL SOURCE:
         (A) ORGANISM: Homo sapiens (xi) SEQUENCE DESCRIPTION: SEQ ID NO:2:

His Xaa Cys Xaa Xaa Xaa Cys His Xaa Gly Xaa Cys
1               5                   10

(2) INFORMATION FOR SEQ ID NO:3:

(i) SEQUENCE CHARACTERISTICS:
         (A) LENGTH: 21 base pairs
         (B) TYPE: nucleic acid
         (C) STRANDEDNESS: double
         (D) TOPOLOGY: linear (ii) MOLECULE TYPE: cDNA (vi) ORIGINAL SOURCE:
         (A) ORGANISM: Homo sapiens (xi) SEQUENCE DESCRIPTION: SEQ ID NO:3:

CCCTTCCCCT AGCAACAGAT G                                                   21

(2) INFORMATION FOR SEQ ID NO:4:

(i) SEQUENCE CHARACTERISTICS:
         (A) LENGTH: 3509 base pairs
         (B) TYPE: nucleic acid
         (C) STRANDEDNESS: double
         (D) TOPOLOGY: linear (ii) MOLECULE TYPE: cDNA
```

(vi) ORIGINAL SOURCE:
    (A) ORGANISM: Homo sapiens (ix) FEATURE:
    (A) NAME/KEY: CDS
    (B) LOCATION: 1..3312

(xi) SEQUENCE DESCRIPTION: SEQ ID NO:4:

```
ATG GAA TTC AGC AGC ATC TGT ATT GAA TTT AAA AGT ACC TTG AGA CAG          48
Met Glu Phe Ser Ser Ile Cys Ile Glu Phe Lys Ser Thr Leu Arg Gln
 1               5                  10                  15

GAG GCG CCT CCG CCA TCC CGT GCC GCA GAA CCT AGA TCG AGC TGT ACA          96
Glu Ala Pro Pro Pro Ser Arg Ala Ala Glu Pro Arg Ser Ser Cys Thr
             20                  25                  30

GTT CAC CAC CTC CCT GTC ACC TTT CCA GGC AGG TCC CTT ATG ATG AAA         144
Val His His Leu Pro Val Thr Phe Pro Gly Arg Ser Leu Met Met Lys
         35                  40                  45

TCT CTG CTG TTC ATC AGC ATA GTT ATC ATC CGT CAG GAA GGC AAA CCT         192
Ser Leu Leu Phe Ile Ser Ile Val Ile Ile Arg Gln Glu Gly Lys Pro
 50                  55                  60

AAG AGT CAG CAG ACG TCT TTC CAG TCC TCT CCT TGT AAT AAA TCG CCC         240
Lys Ser Gln Gln Thr Ser Phe Gln Ser Ser Pro Cys Asn Lys Ser Pro
 65                  70                  75                  80

AAG AGC CAT GGC CTT CAG AAT CAA CCT TGG CAG AAA TTG AGG AAT GAG         288
Lys Ser His Gly Leu Gln Asn Gln Pro Trp Gln Lys Leu Arg Asn Glu
             85                  90                  95

AAG CAC CAT ATC AGA GTC AAG AAA GCA CAG AGT CTT GCT GAG CAG ACC         336
Lys His His Ile Arg Val Lys Lys Ala Gln Ser Leu Ala Glu Gln Thr
            100                 105                 110

TCA GAT ACA GCT GGA TTA GAG AGC TCG ACC AGA TCA GAG AGT GGG ACA         384
Ser Asp Thr Ala Gly Leu Glu Ser Ser Thr Arg Ser Glu Ser Gly Thr
        115                 120                 125

GAC CTC AGA GAG CAT AGT CCT TCT GAG AGT GAG AAG GAA GTT GTG GGT         432
Asp Leu Arg Glu His Ser Pro Ser Glu Ser Glu Lys Glu Val Val Gly
    130                 135                 140

GCA GAT CCC AGG GGA GCA AAA CCC AAA AAA GCA ACA CAG TTT GTA TAC         480
Ala Asp Pro Arg Gly Ala Lys Pro Lys Lys Ala Thr Gln Phe Val Tyr
145                 150                 155                 160

AGC TAT GCT AGA GGA CCA AAA GTC AAG GAG AAA CTC AAA TGT GAA TGG         528
Ser Tyr Ala Arg Gly Pro Lys Val Lys Glu Lys Leu Lys Cys Glu Trp
                165                 170                 175

AGT AAC CGA ACA ACT CCA AAA CCG GAG ATG CTG GAC CCG AAA GTA CCA         576
Ser Asn Arg Thr Thr Pro Lys Pro Glu Met Leu Asp Pro Lys Val Pro
            180                 185                 190

AAC CTG TGG GGG TTT TCC ACC CTG ACT CTT CAG AGG CAT CCT CTA GAA         624
Asn Leu Trp Gly Phe Ser Thr Leu Thr Leu Gln Arg His Pro Leu Glu
        195                 200                 205

AAG GAG TAT TGG ATG GGT ATG GAG CCA GAC GAA ATG AGC AGA GAA GAT         672
Lys Glu Tyr Trp Met Gly Met Glu Pro Asp Glu Met Ser Arg Glu Asp
    210                 215                 220

ACC CAC AGA AAA GGC CTC CCT GGG AAG TGG AGG GGG CCA GGC CAC GAC         720
Thr His Arg Lys Gly Leu Pro Gly Lys Trp Arg Gly Pro Gly His Asp
225                 230                 235                 240

CAG GCA GAA ATC CAC CAA AAC AGG AGG GCC ACC GAC ATA CAA ACG CAG         768
Gln Ala Glu Ile His Gln Asn Arg Arg Ala Thr Asp Ile Gln Thr Gln
                245                 250                 255

GAC ACA GAA ACA ACA TGG GCC CCA TTC CAA AGT GAT GAC CTC AAT GAA         816
Asp Thr Glu Thr Thr Trp Ala Pro Phe Gln Ser Asp Asp Leu Asn Glu
            260                 265                 270

AGA CCA GCA AAA TCT ACC TGT GAC AGT GAG AAC TTG GCA GTC ATC AAC         864
Arg Pro Ala Lys Ser Thr Cys Asp Ser Glu Asn Leu Ala Val Ile Asn
```

-continued

```
                   275                    280                     285
AAG TCT TCC AGG AGG GTT GAC CCA GAG AAA TGC ACT GTA CGG AGG CAG         912
Lys Ser Ser Arg Arg Val Asp Pro Glu Lys Cys Thr Val Arg Arg Gln
    290                     295                     300

GAT CCT CAA GTA GTA TCT CCT TTC TCC CGA GGC AAA CAG AAC CAT GTG         960
Asp Pro Gln Val Val Ser Pro Phe Ser Arg Gly Lys Gln Asn His Val
305                     310                     315                 320

CTA AAG AAT GTG GAA ACG CAC ACA GGT TCT CTA ATT GAA CAA CTA ACA        1008
Leu Lys Asn Val Glu Thr His Thr Gly Ser Leu Ile Glu Gln Leu Thr
                325                     330                     335

ACA GAA AAA TAC GAG TGC ATG GTG TGC TGT GAA TTG GTT CGT GTC ACG        1056
Thr Glu Lys Tyr Glu Cys Met Val Cys Cys Glu Leu Val Arg Val Thr
            340                     345                     350

GCC CCA GTG TGG AGT TGT CAG AGC TGT TAC CAT GTG TTT CAT TTG AAC        1104
Ala Pro Val Trp Ser Cys Gln Ser Cys Tyr His Val Phe His Leu Asn
                355                     360                     365

TGC ATA AAG AAA TGG GCA AGG TCT CCA GCA TCT CAA GCA GAT GGC CAG        1152
Cys Ile Lys Lys Trp Ala Arg Ser Pro Ala Ser Gln Ala Asp Gly Gln
370                     375                     380

AGT GGT TGG AGG TGC CCT GCC TGT CAG AAT GTT TCT GCA CAT GTT CCT        1200
Ser Gly Trp Arg Cys Pro Ala Cys Gln Asn Val Ser Ala His Val Pro
385                     390                     395                 400

AAT ACC TTC TCT TGT TTC TGT GGC AAG GTA AAG AAT CCT GAG TGG AGC        1248
Asn Thr Phe Ser Cys Phe Cys Gly Lys Val Lys Asn Pro Glu Trp Ser
                405                     410                     415

AGA AAT GAA ATT CCA CAT AGC TGT GGT GAG GTT TGT AGA AAG AAA CAG        1296
Arg Asn Glu Ile Pro His Ser Cys Gly Glu Val Cys Arg Lys Lys Gln
            420                     425                     430

CCT GGC CAG GAC TGC CCA CAT TCC TGT AAC CTT CTC TGC CAT CCA GGA        1344
Pro Gly Gln Asp Cys Pro His Ser Cys Asn Leu Leu Cys His Pro Gly
                435                     440                     445

CCC TGC CCA CCC TGC CCT GCC TTT ATG ACA AAA ACA TGT GAA TGT GGA        1392
Pro Cys Pro Pro Cys Pro Ala Phe Met Thr Lys Thr Cys Glu Cys Gly
            450                     455                     460

CGA ACC AGG CAC ACA GTT CGC TGT GGT CAG GCT GTC TCA GTC CAC TGT        1440
Arg Thr Arg His Thr Val Arg Cys Gly Gln Ala Val Ser Val His Cys
465                     470                     475                 480

TCT AAC CCA TGT GAG AAT ATT TTG AAC TGT GGT CAG CAC CAG TGT GCT        1488
Ser Asn Pro Cys Glu Asn Ile Leu Asn Cys Gly Gln His Gln Cys Ala
                485                     490                     495

GAG CTG TGC CAT GGG GGT CAG TGC CAG CCT TGC CAG ATC ATT TTG AAC        1536
Glu Leu Cys His Gly Gly Gln Cys Gln Pro Cys Gln Ile Ile Leu Asn
            500                     505                     510

CAG GTA TGC TAT TGC GGC AGC ACC TCC CGA GAT GTG TTA TGT GGA ACC        1584
Gln Val Cys Tyr Cys Gly Ser Thr Ser Arg Asp Val Leu Cys Gly Thr
                515                     520                     525

GAT GTA GGA AAG TCT GAT GGA TTT GGG GAT TTC AGC TGT TTA AAG ACA        1632
Asp Val Gly Lys Ser Asp Gly Phe Gly Asp Phe Ser Cys Leu Lys Thr
            530                     535                     540

TGT GGC AAG GAC TTG AAA TGC GGT AAC CAT ACA TGT TCG CAA GTG TGC        1680
Cys Gly Lys Asp Leu Lys Cys Gly Asn His Thr Cys Ser Gln Val Cys
545                     550                     555                 560

CAC CCT CAG CCC TGC CAG CAA TGC CCA CGG CTC CCC CAG CTG GTG CGC        1728
His Pro Gln Pro Cys Gln Gln Cys Pro Arg Leu Pro Gln Leu Val Arg
                565                     570                     575

TGT TGC CCC TGT GGC CAA ACT CCT CTC AGC CAA TTG CTA GAA CTT GGA        1776
Cys Cys Pro Cys Gly Gln Thr Pro Leu Ser Gln Leu Leu Glu Leu Gly
            580                     585                     590

AGT AGT AGT CGG AAA ACA TGC ATG GAC CCT GTG CCT TCA TGT GGA AAA        1824
Ser Ser Ser Arg Lys Thr Cys Met Asp Pro Val Pro Ser Cys Gly Lys
```

-continued

|     |     |     |     |     |     |     |
|---|---|---|---|---|---|---|
| | 595 | | 600 | | 605 | |

```
GTG TGC GGC AAG CCT CTG CCT TGT GGT TCC TTA GAT TTC ATT CAT ACC     1872
Val Cys Gly Lys Pro Leu Pro Cys Gly Ser Leu Asp Phe Ile His Thr
610             615                 620

TGT GAA AAG CTC TGC CAT GAA GGA GAC TGT GGA CCA GTC TCT CGC ACA     1920
Cys Glu Lys Leu Cys His Glu Gly Asp Cys Gly Pro Val Ser Arg Thr
625                 630                 635                 640

TCA GTT ATT TCC TGC AGA TGC TCT TTC AGA ACA AAG GAG CTT CCA TGT     1968
Ser Val Ile Ser Cys Arg Cys Ser Phe Arg Thr Lys Glu Leu Pro Cys
            645                 650                 655

ACC AGT CTC AAA AGT GAA GAT GCT ACA TTT ATG TGT GAC AAG CGG TGT     2016
Thr Ser Leu Lys Ser Glu Asp Ala Thr Phe Met Cys Asp Lys Arg Cys
            660                 665                 670

AAC AAG AAA CGG TTG TGT GGA CGG CAT AAA TGT AAT GAG ATA TGC TGT     2064
Asn Lys Lys Arg Leu Cys Gly Arg His Lys Cys Asn Glu Ile Cys Cys
            675                 680                 685

GTG GAT AAG GAG CAC AAG TGT CCT TTG AAT TGT GGG AGG AAA CTC CGT     2112
Val Asp Lys Glu His Lys Cys Pro Leu Asn Cys Gly Arg Lys Leu Arg
690                 695                 700

TGT GGC CTT CAT AGG TGT GAA GAA CCT TGT CAT CGT GGA AAC TGC CAG     2160
Cys Gly Leu His Arg Cys Glu Glu Pro Cys His Arg Gly Asn Cys Gln
705                 710                 715                 720

ACA TGC TGG CAA GCC AGT TTT GAT GAA TTA ACC TGC CAT TGT GGT GCA     2208
Thr Cys Trp Gln Ala Ser Phe Asp Glu Leu Thr Cys His Cys Gly Ala
                725                 730                 735

TCA GTG ATT TAC CCT CCA GTT CCC TGT GGT ACT AGG CCC CCT GAA TGT     2256
Ser Val Ile Tyr Pro Pro Val Pro Cys Gly Thr Arg Pro Pro Glu Cys
            740                 745                 750

ACC CAA ACC TGC GCT AGA GTC CAT GAG TGT GAC CAT CCA GTA TAT CAT     2304
Thr Gln Thr Cys Ala Arg Val His Glu Cys Asp His Pro Val Tyr His
            755                 760                 765

TCT GGT CAT AGT GAG GAG AAG TGT CCC CCT TGC ACT TTC CTA ACT CAG     2352
Ser Gly His Ser Glu Glu Lys Cys Pro Pro Cys Thr Phe Leu Thr Gln
770                 775                 780

AAG TGG TGC ATG GGC AAG CAT GAG TTT CGG AGC AAC ATC CCC TGT CAC     2400
Lys Trp Cys Met Gly Lys His Glu Phe Arg Ser Asn Ile Pro Cys His
785                 790                 795                 800

CTG GTT GAT ATC TCT TGC GGA TTA CCC TGC AGT GCC ACG CTA CCA TGT     2448
Leu Val Asp Ile Ser Cys Gly Leu Pro Cys Ser Ala Thr Leu Pro Cys
                805                 810                 815

GGG ATG CAC AAA TGT CAG AGA CTC TGT CAC AAA GGG GAG TGT CTT GTG     2496
Gly Met His Lys Cys Gln Arg Leu Cys His Lys Gly Glu Cys Leu Val
            820                 825                 830

GAT GAG CCC TGC AAG CAG CCC TGC ACC ACC CCC AGA GCT GAC TGT GGG     2544
Asp Glu Pro Cys Lys Gln Pro Cys Thr Thr Pro Arg Ala Asp Cys Gly
            835                 840                 845

CAC CCC TGT ATG GCA CCC TGC CAT ACC AGC TCA CCC TGC CCT GTG ACT     2592
His Pro Cys Met Ala Pro Cys His Thr Ser Ser Pro Cys Pro Val Thr
850                 855                 860

GCT TGT AAA GCT AAG GTA GAG CTA CAG TGT GAA TGT GGA CGA AGA AAA     2640
Ala Cys Lys Ala Lys Val Glu Leu Gln Cys Glu Cys Gly Arg Arg Lys
865                 870                 875                 880

GAG ATG GTG ATT TGC TCT GAA GCA TCT AGT ACT TAT CAA AGA ATA GCT     2688
Glu Met Val Ile Cys Ser Glu Ala Ser Ser Thr Tyr Gln Arg Ile Ala
                885                 890                 895

GCA ATC TCC ATG GCC TCT AAG ATA ACA GAC ATG CAG CTT GGA GGT TCA     2736
Ala Ile Ser Met Ala Ser Lys Ile Thr Asp Met Gln Leu Gly Gly Ser
            900                 905                 910

GTG GAG ATC AGC AAG TTA ATT ACC AAA AAG GAA GTT CAT CAA GCC AGG     2784
Val Glu Ile Ser Lys Leu Ile Thr Lys Lys Glu Val His Gln Ala Arg
```

```
                    915                 920                 925
CTG GAG TGT GAT GAG GAG TGT TCA GCC TTG GAA AGG AAA AAG AGA TTA    2832
Leu Glu Cys Asp Glu Glu Cys Ser Ala Leu Glu Arg Lys Lys Arg Leu
    930                 935                 940

GCA GAG GCA TTT CAT ATC AGT GAG GAT TCT GAT CCT TTC AAT ATA CGT    2880
Ala Glu Ala Phe His Ile Ser Glu Asp Ser Asp Pro Phe Asn Ile Arg
945                 950                 955                 960

TCT TCA GGG TCA AAA TTC AGT GAT AGT TTG AAA GAA GAT GCC AGG AAG    2928
Ser Ser Gly Ser Lys Phe Ser Asp Ser Leu Lys Glu Asp Ala Arg Lys
                965                 970                 975

GAC TTA AAG TTT GTC AGT GAC GTT GAG AAG GAA ATG GAA ACC CTC GTG    2976
Asp Leu Lys Phe Val Ser Asp Val Glu Lys Glu Met Glu Thr Leu Val
            980                 985                 990

GAG GCC GTG AAT AAG GGA AAG AAT AGT AAG AAA AGC CAC AGC TTC CCT    3024
Glu Ala Val Asn Lys Gly Lys Asn Ser Lys Lys Ser His Ser Phe Pro
        995                 1000                1005

CCC ATG AAC AGA GAC CAC CGC CGG ATC ATC CAT GAC TTG GCC CAA GTT    3072
Pro Met Asn Arg Asp His Arg Arg Ile Ile His Asp Leu Ala Gln Val
    1010                1015                1020

TAT GGC CTG GAG AGC GTG AGC TAT GAC AGT GAA CCG AAG CGC AAT GTG    3120
Tyr Gly Leu Glu Ser Val Ser Tyr Asp Ser Glu Pro Lys Arg Asn Val
1025                1030                1035                1040

GTG GTC ACT GCC ATC AGG GGG AAG TCC GTT TGT CCT CCT ACC ACG CTG    3168
Val Val Thr Ala Ile Arg Gly Lys Ser Val Cys Pro Pro Thr Thr Leu
                1045                1050                1055

ACA GGT GTG CTT GAA AGG GAA ATG CAG GCA CGG CCT CCA CCA CCG ATT    3216
Thr Gly Val Leu Glu Arg Glu Met Gln Ala Arg Pro Pro Pro Pro Ile
            1060                1065                1070

CCT CAT CAC AGA CAT CAG TCA GAC AAG AAT CCT GGG AGC AGT AAT TTA    3264
Pro His His Arg His Gln Ser Asp Lys Asn Pro Gly Ser Ser Asn Leu
        1075                1080                1085

CAG AAA ATA ACC AAG GAG CCA ATA ATT GAC TAT TTT GAC GTC CAG GAC    3312
Gln Lys Ile Thr Lys Glu Pro Ile Ile Asp Tyr Phe Asp Val Gln Asp
    1090                1095                1100

TAAGAAGATC ATGATGCACT TAGATAAAAG AATGATTAGG TATAGTGGAG ACTTATTTGC    3372

CAGCAGATAA ATCATGCCCG TTCCCCTCTG CCTGGCAGAA TCACAGTCTC ACATACTGTC    3432

TTGTACTGAC ACATCCAAAG CATGAGTGTG TCAGAAATCC CTTGTCTATT CCTGTCTGTA    3492

TAAAGTGTTT CAGGATG                                                    3509

(2) INFORMATION FOR SEQ ID NO:5:

(i) SEQUENCE CHARACTERISTICS:
        (A) LENGTH: 1104 amino acids
        (B) TYPE: amino acid
        (D) TOPOLOGY: linear (ii) MOLECULE TYPE: protein (xi) SEQUENCE DESCRIPTION: SEQ ID NO:5:

Met Glu Phe Ser Ser Ile Cys Ile Glu Phe Lys Ser Thr Leu Arg Gln
1               5                   10                  15

Glu Ala Pro Pro Pro Ser Arg Ala Ala Glu Pro Arg Ser Ser Cys Thr
            20                  25                  30

Val His His Leu Pro Val Thr Phe Pro Gly Arg Ser Leu Met Met Lys
        35                  40                  45

Ser Leu Leu Phe Ile Ser Ile Val Ile Ile Arg Gln Glu Gly Lys Pro
    50                  55                  60

Lys Ser Gln Gln Thr Ser Phe Gln Ser Ser Pro Cys Asn Lys Ser Pro
65              70                  75                  80
```

```
Lys Ser His Gly Leu Gln Asn Gln Pro Trp Gln Lys Leu Arg Asn Glu
             85                  90                  95

Lys His His Ile Arg Val Lys Lys Ala Gln Ser Leu Ala Glu Gln Thr
            100                 105                 110

Ser Asp Thr Ala Gly Leu Glu Ser Ser Thr Arg Ser Glu Ser Gly Thr
            115                 120                 125

Asp Leu Arg Glu His Ser Pro Ser Glu Ser Glu Lys Glu Val Val Gly
            130                 135                 140

Ala Asp Pro Arg Gly Ala Lys Pro Lys Lys Ala Thr Gln Phe Val Tyr
145                 150                 155                 160

Ser Tyr Ala Arg Gly Pro Lys Val Lys Glu Lys Leu Lys Cys Glu Trp
                165                 170                 175

Ser Asn Arg Thr Thr Pro Lys Pro Glu Met Leu Asp Pro Lys Val Pro
            180                 185                 190

Asn Leu Trp Gly Phe Ser Thr Leu Thr Leu Gln Arg His Pro Leu Glu
            195                 200                 205

Lys Glu Tyr Trp Met Gly Met Glu Pro Asp Glu Met Ser Arg Glu Asp
            210                 215                 220

Thr His Arg Lys Gly Leu Pro Gly Lys Trp Arg Gly Pro Gly His Asp
225                 230                 235                 240

Gln Ala Glu Ile His Gln Asn Arg Arg Ala Thr Asp Ile Gln Thr Gln
                245                 250                 255

Asp Thr Glu Thr Thr Trp Ala Pro Phe Gln Ser Asp Asp Leu Asn Glu
            260                 265                 270

Arg Pro Ala Lys Ser Thr Cys Asp Ser Glu Asn Leu Ala Val Ile Asn
            275                 280                 285

Lys Ser Ser Arg Arg Val Asp Pro Glu Lys Cys Thr Val Arg Arg Gln
            290                 295                 300

Asp Pro Gln Val Val Ser Pro Phe Ser Arg Gly Lys Gln Asn His Val
305                 310                 315                 320

Leu Lys Asn Val Glu Thr His Thr Gly Ser Leu Ile Glu Gln Leu Thr
                325                 330                 335

Thr Glu Lys Tyr Glu Cys Met Val Cys Cys Glu Leu Val Arg Val Thr
            340                 345                 350

Ala Pro Val Trp Ser Cys Gln Ser Cys Tyr His Val Phe His Leu Asn
            355                 360                 365

Cys Ile Lys Lys Trp Ala Arg Ser Pro Ala Ser Gln Ala Asp Gly Gln
370                 375                 380

Ser Gly Trp Arg Cys Pro Ala Cys Gln Asn Val Ser Ala His Val Pro
385                 390                 395                 400

Asn Thr Phe Ser Cys Phe Cys Gly Lys Val Lys Asn Pro Glu Trp Ser
                405                 410                 415

Arg Asn Glu Ile Pro His Ser Cys Gly Glu Val Cys Arg Lys Lys Gln
            420                 425                 430

Pro Gly Gln Asp Cys Pro His Ser Cys Asn Leu Leu Cys His Pro Gly
            435                 440                 445

Pro Cys Pro Pro Cys Pro Ala Phe Met Thr Lys Thr Cys Glu Cys Gly
            450                 455                 460

Arg Thr Arg His Thr Val Arg Cys Gly Gln Ala Val Ser Val His Cys
465                 470                 475                 480

Ser Asn Pro Cys Glu Asn Ile Leu Asn Cys Gly Gln His Gln Cys Ala
                485                 490                 495

Glu Leu Cys His Gly Gly Gln Cys Gln Pro Cys Gln Ile Ile Leu Asn
```

-continued

```
              500                 505                 510
Gln Val Cys Tyr Cys Gly Ser Thr Ser Arg Asp Val Leu Cys Gly Thr
            515                 520                 525
Asp Val Gly Lys Ser Asp Gly Phe Gly Asp Phe Ser Cys Leu Lys Thr
            530                 535                 540
Cys Gly Lys Asp Leu Lys Cys Gly Asn His Thr Cys Ser Gln Val Cys
545                 550                 555                 560
His Pro Gln Pro Cys Gln Cys Pro Arg Leu Pro Gln Leu Val Arg
            565                 570                 575
Cys Cys Pro Cys Gly Gln Thr Pro Leu Ser Gln Leu Glu Leu Gly
            580                 585                 590
Ser Ser Ser Arg Lys Thr Cys Met Asp Pro Val Pro Ser Cys Gly Lys
            595                 600                 605
Val Cys Gly Lys Pro Leu Pro Cys Gly Ser Leu Asp Phe Ile His Thr
            610                 615                 620
Cys Glu Lys Leu Cys His Glu Gly Asp Cys Gly Pro Val Ser Arg Thr
625                 630                 635                 640
Ser Val Ile Ser Cys Arg Cys Ser Phe Arg Thr Lys Glu Leu Pro Cys
            645                 650                 655
Thr Ser Leu Lys Ser Glu Asp Ala Thr Phe Met Cys Asp Lys Arg Cys
            660                 665                 670
Asn Lys Lys Arg Leu Cys Gly Arg His Lys Cys Asn Glu Ile Cys Cys
            675                 680                 685
Val Asp Lys Glu His Lys Cys Pro Leu Asn Cys Gly Arg Lys Leu Arg
            690                 695                 700
Cys Gly Leu His Arg Cys Glu Glu Pro Cys His Arg Gly Asn Cys Gln
705                 710                 715                 720
Thr Cys Trp Gln Ala Ser Phe Asp Glu Leu Thr Cys His Cys Gly Ala
            725                 730                 735
Ser Val Ile Tyr Pro Pro Val Pro Cys Gly Thr Arg Pro Pro Glu Cys
            740                 745                 750
Thr Gln Thr Cys Ala Arg Val His Glu Cys Asp His Pro Val Tyr His
            755                 760                 765
Ser Gly His Ser Glu Glu Lys Cys Pro Pro Cys Thr Phe Leu Thr Gln
            770                 775                 780
Lys Trp Cys Met Gly Lys His Glu Phe Arg Ser Asn Ile Pro Cys His
785                 790                 795                 800
Leu Val Asp Ile Ser Cys Gly Leu Pro Cys Ser Ala Thr Leu Pro Cys
            805                 810                 815
Gly Met His Lys Cys Gln Arg Leu Cys His Lys Gly Glu Cys Leu Val
            820                 825                 830
Asp Glu Pro Cys Lys Gln Pro Cys Thr Thr Pro Arg Ala Asp Cys Gly
            835                 840                 845
His Pro Cys Met Ala Pro Cys His Thr Ser Pro Cys Pro Val Thr
            850                 855                 860
Ala Cys Lys Ala Lys Val Glu Leu Gln Cys Glu Cys Gly Arg Arg Lys
865                 870                 875                 880
Glu Met Val Ile Cys Ser Glu Ala Ser Ser Thr Tyr Gln Arg Ile Ala
            885                 890                 895
Ala Ile Ser Met Ala Ser Lys Ile Thr Asp Met Gln Leu Gly Gly Ser
            900                 905                 910
Val Glu Ile Ser Lys Leu Ile Thr Lys Lys Glu Val His Gln Ala Arg
            915                 920                 925
```

```
Leu Glu Cys Asp Glu Glu Cys Ser Ala Leu Glu Arg Lys Lys Arg Leu
    930                 935                 940

Ala Glu Ala Phe His Ile Ser Glu Asp Ser Asp Pro Phe Asn Ile Arg
945                 950                 955                 960

Ser Ser Gly Ser Lys Phe Ser Asp Ser Leu Lys Glu Asp Ala Arg Lys
            965                 970                 975

Asp Leu Lys Phe Val Ser Asp Val Glu Lys Glu Met Glu Thr Leu Val
        980                 985                 990

Glu Ala Val Asn Lys Gly Lys Asn Ser Lys Lys Ser His Ser Phe Pro
    995                 1000                1005

Pro Met Asn Arg Asp His Arg Arg Ile Ile His Asp Leu Ala Gln Val
    1010                1015                1020

Tyr Gly Leu Glu Ser Val Ser Tyr Asp Ser Glu Pro Leu Arg Asn Val
1025                1030                1035                1040

Val Val Thr Ala Ile Arg Gly Lys Ser Val Cys Pro Pro Thr Thr Leu
            1045                1050                1055

Thr Gly Val Leu Glu Arg Glu Met Gln Ala Arg Pro Pro Pro Pro Ile
        1060                1065                1070

Pro His His Arg His Gln Ser Asp Lys Asn Pro Gly Ser Ser Asn Leu
    1075                1080                1085

Gln Lys Ile Thr Lys Glu Pro Ile Ile Asp Tyr Phe Asp Val Gln Asp
    1090                1095                1100
```

(2) INFORMATION FOR SEQ ID NO:6:

(i) SEQUENCE CHARACTERISTICS:
        (A) LENGTH: 14 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: homo sapiens (xi) SEQUENCE DESCRIPTION: SEQ ID NO:6:

CCTAGCAACA GATG                          14

(2) INFORMATION FOR SEQ ID NO:7:

(i) SEQUENCE CHARACTERISTICS:
        (A) LENGTH: 7 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: homo sapiens (xi) SEQUENCE DESCRIPTION: SEQ ID NO:7:

CGTCATC                                7

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: cDNA

```
        (vi) ORIGINAL SOURCE:
             (A) ORGANISM: homo sapiens (xi) SEQUENCE DESCRIPTION: SEQ ID NO:8:

AAAATCTGCC CAGAGACAGA TGAGGTCCTT                                           30

(2) INFORMATION FOR SEQ ID NO:9:

(i) SEQUENCE CHARACTERISTICS:
             (A) LENGTH: 30 base pairs
             (B) TYPE: nucleic acid
             (C) STRANDEDNESS: double
             (D) TOPOLOGY: linear (ii) MOLECULE TYPE: cDNA (vi) ORIGINAL SOURCE:
             (A) ORGANISM: homo sapiens (xi) SEQUENCE DESCRIPTION: SEQ ID NO:9:

ACTTTCTGCC TAGTGAGCAA TGACTCATAC                                           30

(2) INFORMATION FOR SEQ ID NO:10:

(i) SEQUENCE CHARACTERISTICS:
             (A) LENGTH: 23 base pairs
             (B) TYPE: nucleic acid
             (C) STRANDEDNESS: double
             (D) TOPOLOGY: linear (ii) MOLECULE TYPE: cDNA (vi) ORIGINAL SOURCE:
             (A) ORGANISM: homo sapiens (xi) SEQUENCE DESCRIPTION: SEQ ID NO:10:

TGTGTCCTGG ACCCTTTGCA AGA                                                  23

(2) INFORMATION FOR SEQ ID NO:11:

(i) SEQUENCE CHARACTERISTICS:
             (A) LENGTH: 27 base pairs
             (B) TYPE: nucleic acid
             (C) STRANDEDNESS: double
             (D) TOPOLOGY: linear (ii) MOLECULE TYPE: cDNA (vi) ORIGINAL SOURCE:
             (A) ORGANISM: homo sapiens (xi) SEQUENCE DESCRIPTION: SEQ ID NO:11:

AAATATTTTT CTGATTGGCC AAAGAGT                                              27

(2) INFORMATION FOR SEQ ID NO:12:

(i) SEQUENCE CHARACTERISTICS:
             (A) LENGTH: 22 base pairs
             (B) TYPE: nucleic acid
             (C) STRANDEDNESS: double
             (D) TOPOLOGY: linear (ii) MOLECULE TYPE: cDNA (vi) ORIGINAL SOURCE:
             (A) ORGANISM: homo sapiens (xi) SEQUENCE DESCRIPTION: SEQ ID NO:12:

ATTCGATCGG GGCGGGGCGA GC                                                   22
```

-continued (2) INFORMATION FOR SEQ ID NO:13:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: homo sapiens (xi) SEQUENCE DESCRIPTION: SEQ ID NO:13:

GTGGGAAATT CCGTGGGAAA TTCCG                    25

(2) INFORMATION FOR SEQ ID NO:14:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: homo sapiens (xi) SEQUENCE DESCRIPTION: SEQ ID NO:14:

Glu Arg Lys Arg Ala
1             5

(2) INFORMATION FOR SEQ ID NO:15:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: homo sapiens (xi) SEQUENCE DESCRIPTION: SEQ ID NO:15:

Lys Glu Asp Ala Arg Lys Asp
1             5

(2) INFORMATION FOR SEQ ID NO:16:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: homo sapiens (xi) SEQUENCE DESCRIPTION: SEQ ID NO:16:

Ser Glu Ser Glu Lys Glu
1             5